(12) United States Patent
Hallak et al.

(10) Patent No.: US 8,889,627 B2
(45) Date of Patent: Nov. 18, 2014

(54) TREATMENT OF MULTIPLE SCLEROSIS WITH COMBINATION OF LAQUINIMOD AND FINGOLIMOD

(71) Applicant: Teva Pharmaceutical Industries, Ltd., Petach-Tikva (IL)

(72) Inventors: Hussein Hallak, East Jerusalem (IL); Nora Tarcic, Modiin (IL); Joel Flaxman Kaye, Netanya (IL)

(73) Assignee: Teva Pharmaceutical Industries, Ltd., Petach-Tikva (IL)

( * ) Notice: Subject to any disclaimer, the term of this patent is extended or adjusted under 35 U.S.C. 154(b) by 0 days.

(21) Appl. No.: 13/650,060

(22) Filed: Oct. 11, 2012

(65) Prior Publication Data

US 2013/0096158 A1    Apr. 18, 2013

Related U.S. Application Data

(60) Provisional application No. 61/546,102, filed on Oct. 12, 2011.

(51) Int. Cl.
| | |
|---|---|
| A61K 38/00 | (2006.01) |
| C07K 14/47 | (2006.01) |
| A01N 43/42 | (2006.01) |
| A61K 31/47 | (2006.01) |
| A01N 33/02 | (2006.01) |
| A61K 31/135 | (2006.01) |
| A61K 31/4704 | (2006.01) |
| A61K 31/137 | (2006.01) |

(52) U.S. Cl.
CPC ........... *A61K 31/4704* (2013.01); *A61K 31/137* (2013.01)
USPC ........................... 514/17.9; 514/312; 514/653

(58) Field of Classification Search
None
See application file for complete search history.

(56) References Cited

U.S. PATENT DOCUMENTS

| | | | |
|---|---|---|---|
| 3,024,257 A | 3/1962 | Millar et al. | |
| 4,107,310 A | 8/1978 | Allais et al. | |
| 4,547,511 A | 10/1985 | Erikshoo et al. | |
| 4,628,053 A | 12/1986 | Fries et al. | |
| 4,738,971 A | 4/1988 | Erikshoo et al. | |
| 4,782,155 A | 11/1988 | Nakagawa et al. | |
| 5,139,878 A | 8/1992 | Kim et al. | |
| 5,716,638 A | 2/1998 | Toutou | |
| 5,719,176 A * | 2/1998 | Fujita et al. | 514/440 |
| 5,912,349 A | 6/1999 | Sih | |
| 6,077,851 A | 6/2000 | Bjork et al. | |
| 6,121,287 A | 9/2000 | Bjork et al. | |
| 6,133,285 A | 10/2000 | Bjork et al. | |
| 6,307,050 B1 | 10/2001 | Kwiatkowski | |
| 6,395,750 B1 | 5/2002 | Hedlund et al. | |
| 6,593,343 B2 | 7/2003 | Bjork et al. | |
| 6,605,616 B1 | 8/2003 | Bjork et al. | |
| 6,696,407 B1 | 2/2004 | Longo et al. | |
| 6,802,422 B2 | 10/2004 | Kalvelage et al. | |
| 6,875,869 B2 | 4/2005 | Jansson | |
| 7,485,311 B2 | 2/2009 | Lue et al. | |
| 7,560,100 B2 | 7/2009 | Pinchasi et al. | |
| 7,560,557 B2 | 7/2009 | Jansson | |
| 7,589,208 B2 | 9/2009 | Jansson et al. | |
| 7,884,208 B2 | 2/2011 | Frenkel et al. | |
| 7,989,473 B2 * | 8/2011 | Patashnik et al. | 514/312 |
| 8,178,127 B2 | 5/2012 | Safadi et al. | |
| 8,236,778 B2 * | 8/2012 | vila Zaragoza et al. | 514/46 |
| 8,252,933 B2 | 8/2012 | Gant et al. | |
| 8,314,124 B2 | 11/2012 | Jansson et al. | |
| 2002/0173520 A1 | 11/2002 | Bjork et al. | |
| 2003/0087929 A1 | 5/2003 | Kimura et al. | |
| 2003/0119826 A1 | 6/2003 | Manning et al. | |
| 2003/0124187 A1 | 7/2003 | Mention et al. | |
| 2004/0247673 A1 | 12/2004 | Fergione et al. | |
| 2005/0074451 A1 | 4/2005 | Yednock et al. | |
| 2005/0271717 A1 | 12/2005 | Berchielli et al. | |
| 2006/0004019 A1 | 1/2006 | Lieberburg | |
| 2006/0183105 A1 | 8/2006 | Aiyar et al. | |

(Continued)

FOREIGN PATENT DOCUMENTS

| | | |
|---|---|---|
| EP | 1073639 | 11/2002 |
| EP | 1097139 | 12/2002 |

(Continued)

OTHER PUBLICATIONS

Martinez-Forero et al, Pharmacogenomics of multiple sclerosis: in search for a personalized therapy, 2008, Expert Opin. Pharmacother., 9(17), pp. 3053-3067.*
Nicholas, R et al, Development of oral immunodmodulatory agents in the management of multiple sclerosis, May 9, 2011, Drug Design, Development and Therapy, 5, pp. 255-274.*
Gasperini, C et al, Emerging oral drugs for multiple sclerosis, 2008, Expert Opin. Emerging Drugs, 13(3), pp. 465-477.*
Kappos, L et al, A Placebo-Controlled Trial of Oral Fingolimod in Relapsing Multiple Sclerosis, Feb. 4, 2010, The New England Jounal of Medicine, vol. 362, No. 5, pp. 387-401.*
Costello, et al., Combination therapies for multiple sclerosis: scientific rationale, clinical trials, and clinical practice, 2007, Current Opinion in Neurology, 20, pp. 281-285.*

(Continued)

*Primary Examiner* — Jeffrey S. Lundgren
*Assistant Examiner* — Tori M Strong
(74) *Attorney, Agent, or Firm* — John P. White; Gary J. Gershik; Cooper & Dunham LLP

(57) ABSTRACT

This invention provides a method of treating a subject afflicted with multiple sclerosis or presenting a clinically isolated syndrome comprising administering to the subject laquinimod as an add-on therapy to or in combination with fingolimod. This invention also provides a package and a pharmaceutical composition comprising laquinimod and fingolimod for treating a subject afflicted with multiple sclerosis or presenting a clinically isolated syndrome. This invention also provides laquinimod for use as an add-on therapy or in combination with fingolimod in treating a subject afflicted with multiple sclerosis or presenting a clinically isolated syndrome. This invention further provides use of laquinimod and fingolimod in the preparation of a combination for treating a subject afflicted with multiple sclerosis or presenting a clinically isolated syndrome.

20 Claims, 1 Drawing Sheet

(56) References Cited

U.S. PATENT DOCUMENTS

| | | | |
|---|---|---|---|
| 2007/0086979 | A1 | 4/2007 | Chevrier et al. |
| 2007/0207141 | A1 | 9/2007 | Lieberburg |
| 2007/0231319 | A1 | 10/2007 | Yednock |
| 2007/0280891 | A1 | 12/2007 | Tamarkin et al. |
| 2008/0044382 | A1 | 2/2008 | Lieberburg |
| 2008/0063607 | A1 | 3/2008 | Tamarkin et al. |
| 2008/0090897 | A1 | 4/2008 | Steiner et al. |
| 2008/0108641 | A1 | 5/2008 | Ajami |
| 2008/0118553 | A1 | 5/2008 | Frenkel et al. |
| 2008/0166348 | A1 | 7/2008 | Kupper et al. |
| 2008/0206159 | A1 | 8/2008 | Tamarkin et al. |
| 2009/0048181 | A1 | 2/2009 | Schipper et al. |
| 2009/0062330 | A1 | 3/2009 | Kalafer et al. |
| 2009/0081259 | A1 | 3/2009 | Jonas et al. |
| 2009/0148462 | A1 | 6/2009 | Chevrier et al. |
| 2009/0156542 | A1 | 6/2009 | Purschke et al. |
| 2009/0221575 | A1 | 9/2009 | Gerber et al. |
| 2010/0028297 | A1* | 2/2010 | Stewart et al. ............... 424/85.4 |
| 2010/0158903 | A1 | 6/2010 | Smith et al. |
| 2010/0260716 | A1 | 10/2010 | Stohr et al. |
| 2010/0310547 | A1 | 12/2010 | Soliven |
| 2010/0322900 | A1 | 12/2010 | Tarcic et al. |
| 2011/0015132 | A1 | 1/2011 | Zaragoza |
| 2011/0027219 | A1 | 2/2011 | Tarcic et al. |
| 2011/0034508 | A1 | 2/2011 | Hayardeny |
| 2011/0112141 | A1 | 5/2011 | Frenkel et al. |
| 2011/0118308 | A1 | 5/2011 | Frenkel et al. |
| 2011/0217295 | A1 | 9/2011 | Haviv et al. |
| 2011/0218179 | A1 | 9/2011 | Haviv et al. |
| 2011/0218203 | A1 | 9/2011 | Kaye et al. |
| 2011/0251235 | A1 | 10/2011 | Patashnik et al. |
| 2012/0010238 | A1 | 1/2012 | Piryatinsky et al. |
| 2012/0010239 | A1 | 1/2012 | Fristedt |
| 2012/0142730 | A1 | 6/2012 | Tarcic et al. |
| 2012/0225124 | A1 | 9/2012 | Safadi et al. |
| 2013/0028866 | A1 | 1/2013 | Gilgun et al. |
| 2013/0029916 | A1 | 1/2013 | Gilgun et al. |
| 2013/0203807 | A1 | 8/2013 | Tarcic et al. |
| 2013/0217724 | A1 | 8/2013 | Ioffe at al. |
| 2013/0259856 | A1 | 10/2013 | Kaye |
| 2013/0272996 | A1 | 10/2013 | Tarcic et al. |
| 2013/0303569 | A1 | 11/2013 | Bar-Zohar |

FOREIGN PATENT DOCUMENTS

| | | | |
|---|---|---|---|
| EP | 1095021 | | 9/2003 |
| EP | 1720531 | | 11/2006 |
| EP | 1511732 | | 12/2006 |
| WO | WO 99/55678 | | 11/1999 |
| WO | WO 00/03991 | | 1/2000 |
| WO | WO 00/03992 | | 1/2000 |
| WO | WO 03/106424 | | 12/2003 |
| WO | WO 2005/074899 | | 8/2005 |
| WO | WO 2008/079270 | | 7/2008 |
| WO | WO 2009115634 | A1 * | 9/2009 |
| WO | WO 2010/045265 | | 4/2010 |
| WO | WO 2010/057006 | | 5/2010 |
| WO | WO 2010/070449 | | 6/2010 |
| WO | WO 2010147665 | A1 * | 12/2010 |
| WO | WO 2011/086470 | | 7/2011 |

OTHER PUBLICATIONS

Martinez-Forero, et al., Pharmacogenomics of multiple sclerosis: in search for a personalized therapy, 2008, Expert Opinion, 9(17), pp. 3053-3067.*

Martinez-Forero et al., Pharmcogenomics of multiple sclerosis: in search for a personalized therapy, 2008, Expert Opinion Pharmacother., 9(17), pp. 3053-3067.*

Costello et al., Combination therapies for multiple sclerosis: scientific rationale, clinical trials, and clinical practice, 2007, Current Opinion in Neurology, 20, pp. 281-285.*

PCT International Search Report issued Aug. 19, 2010 in connection with PCT International Application No. PCT/US2010/01759, filed Jun. 18, 2010.

PCT International Search Report issued Oct. 5, 2010 in connection with PCT International Application No. PCT/US2010/02194, filed Aug. 9, 2010.

PCT International Search Report issued Apr. 3, 2012 in connection with PCT/US2011/063460, filed Dec. 6, 2011.

PCT International Preliminary Report on Patentability issued Dec. 20, 2011 in connection with PCT International Application No. PCT/US2010/001759.

PCT International Preliminary Report on Patentability issued Feb. 14, 2012 in connection with PCT International Application No. PCT/US2010/002194.

Written Opinion of the International Searching Authority issued Aug. 19, 2010 in connection with PCT International Application No. PCT/US2010/01759.

Written Opinion of the International Searching Authority issued Oct. 5, 2010 in connection with PCT International Application No. PCT/US2010/02194.

Written Opinion of the International Searching Authority issued Apr. 3, 2012 in connection with PCT/US2011/063460.

PCT International Search Report issued Dec. 7, 2012 in connection with PCT International Application No. PCT/US2012/59733.

Written Opinion of the International Searching Authority issued Dec. 7, 2012 in connection with PCT International Application No. PCT/US2012/59733.

Office Action issued by the U.S. Patent and Trademark Office on Dec. 27, 2011 in connection with U.S. Appl. No. 12/803,121.

May 29, 2012 Amendment filed with the U.S. Patent and Trademark Office on in connection with U.S. Appl. No. 12/803,121.

Final Office Action issued by the U.S. Patent and Trademark Office on Jul. 12, 2012 in connection with U.S. Appl. No. 12/803,121.

Acheson A. et al. (1995). "A BDNF autocrine loop in adult sensory neurons prevents cell death". Nature, 374(6521):450-453.

Alonso M. et al. (2005) "Endogenous BDNF is required for long-term memory formation in the rat parietal cortex". Learning & Memory, 12(5):504-510.

Amaral MD. et al. (2007) "Transient receptor potential channels as novel effectors of brain-derived neurotrophic factor signaling . . ." Pharmacol Ther, 113(2):394-409.

Barkhof F. (1999) "MRI in Multiple Sclerosis: Correlation with Expanded Disability Status Scale (EDSS)", Multiple Sclerosis. 5(4):283-286.

Boneschi et al. (2003) "Effects of glatiramer acetate on relapse rate and accumulated disbility in multiple sclerosis . . ." Multi Scler. 9(4):349-355.

Caffé A. Romeo et al. (2001) "A combination of CNTF and BDNF rescues rd photoreceptors but changes rod differentiation . . ." Investigative Ophthalmology & Visual Science, 42:275.

Chesselet MF. (2003) "Dopamine and Parkinson's disease: is the killer in the house?" Molecular Psychiatry 8(4):369-370.

Ciammola A. et al. (2007) "Low Brain-Derived Neurotrophic Factor (BDNF) Levels in Serum of Huntington's Disease Patients". Am J Med Gent Part B, 144b(4):574-577.

Comi et al. (2007) LAQ/5062 Study Group. "The Effect of Two Doses of Laquinimod on MRI-Monitored Disease Activity . . ." 59th Annual Meeting of the American Academy of Neurology.

Comi et al. (2008) "Effect of laquinimod on MRI-monitored disease activity in patients with relapsing-remitting multiple sclerosis . . ." Lancet. Jun 21, 2008; 371(9630):2085-92.

De Stefano et al. (1999) "Evidence of early axonal damage in patients with multiple sclerosis", Arch Neurol. 2001;58:65-70.

EMEA Guideline on Clinical Investigation of Medicinal Products for the Treatment of Multiple Sclerosis (CPMP/EWP/561/98 Rev. 1, Nov. 2006).

Hohlfeld et al. (2000) "The neuroprotective effect of inflammation: implications for the therapy of multiple sclerosis", J Neuroimmunol. 107(2000):161-166.

Howells DW. et al. (2000) "Reduced BDNF mRNA expression in the Parkinson's disease substantia nigra". Experimental Neurology, 166(1):127-135.

Huang, EJ and Reichardt, LF (2001) "Neurotrophins: roles in neuronal development and function". Annu. Rev. Neurosci, 24:677-736.

(56) References Cited

OTHER PUBLICATIONS

Hyman, C. et al., (1991) "BDNF is a neurotrophic factor for dopaminergic neurons of the substantia nigra". Nature, 350(6315):230-2.

Karussis et al. (1996) "Treatment of secondary progressive multiple sclerosis with the immunomodulator linomide . . ." Neurology. Aug. 1996;47(2):341-6.

Katoh-Semba R. et al. (2002) "Riluzole enhances expression of brain-derived neurotrophic factor with consequent . . ." FASEB J, 16(10):1328-30.

Lehmann et al. (1997) "Inhibition of the progression of multiple sclerosis by linomide is associated with upregulation of CD4+/CD45RA+ . . ." Clin Imm. Immunopathol. 85(2):202-9.

Makar et al. (2008) "Brain derived neurotrophic factor treatment reduces inflammation and apoptosis in experimental allergic encepalomyelitis." J. of the Neuro. 270:70-76.

Miki, Y, et al. (1999) "Relapsing-Remitting Multiple Sclerosis: Longitudinal Analysis of MR Images—Lack of Correlation between Changes in T2 Lesion . . ."Radiology. 213:395-399.

Mix et al. (2008) "Animal models of multiple sclerosis for the development and validation of novel therapies—potential and limitations." Journal of Neurology. 255(6):7-14.

Molteni R, et al. (2006) "Abstract: Chronic treatment with fluoxetine [Prozac® ] up-regulates cellular BDNF mRNA . . ." Int J Neuropsychopharmacol. 9(3):307-17.

Monteggia, LM (2007) "Elucidating the role of brain-derived neurotrophic factor in the brain". Am J Psychiatry, 164(12):1790.

Neuhaus et al. (2003) "Immunomodulation in multiple sclerosis: from immunosuppression to neuroprotection", Trends Pharmacal Sci. 24:131-138.

Noseworthy JH, Lucchinetti C, Rodriguez M, Weinshenker BO. (2000) "Multiple sclerosis", N. Engl J Med. 343:938-952.

Polman et al., (2005) "Diagnostic criteria for multiple sclerosis: 2005 revisions to the McDonald Criteria", Annals of Neurology, vol. 58 Issue 6, pp. 840-846.

Polman et al., (2005) "Treatment with laquinimod reduces development of active MRI lesions in relapsing MS", Neurology. 64:987-991.

Riviere M. (1998) "An analysis of extended survival in patients with amyotrophic lateral sclerosis treated with riluzole". Arch Neurol, 55(4):526-8.

Rudick R. (1999) "Disease-Modifying Drugs for Relapsing-Remitting Multiple Sclerosis and Future Directions for Multiple Sclerosis Therapeutics", Neurotherpatueics. 56:1079-84.

Sandberg-Wollheim et al. (2005) "48-Week Open Safety Study with a High-Dose Oral Laquinimod in MS Patients" Therapy-Immunomodulation—Part II, 15:30-17:00 (Abstract Only).

Sen S. et al. (2008) "Serum brain-derived neurotrophic factor, depression, and antidepressant; medications: meta-analyses and implications". Biol Psychiatry, 64(6):527-532.

Snider et al. (1989) "Neurotrophic molecules". Ann Neurol, 26(4):489-506.

Tramontina JF. et al. (2009) "Brain-derived neurotrophic factor serum levels before and after treatment for acute mania". Neuroscience Letters, 452(2):111-3.

Jan. 23, 2014 Final Office Action issued in connection with U.S. Appl. No. 13/560,851.

Mar. 10, 2014 Response to Oct. 10, 2013 Office Action filed in connection with U.S. Appl. No. 13/560,872.

International Search Report issued Oct. 16, 2012 in connection with PCT International Application No. PCT/US12/048684.

Written Opinion of the International Searching Authority issued Oct. 16, 2012 in connection with PCT International Application No. PCT/US12/048684.

International Search Report issued Oct. 1, 2012 in connection with PCT International Application No. PCT/US12/048689.

Written Opinion of the International Searching Authority issued Oct. 1, 2012 in connection with PCT International Application No. PCT/US12/048689.

International Search Report issued Nov. 27, 2013 in connection with PCT International Application No. PCT/US13/50001.

Written Opinion of the International Searching Authority issued Nov. 27, 2013 in connection with PCT International Application No. PCT/US13/50001.

Mar. 27, 2013 Office Action issued in connection with U.S. Appl. No. 13/560,872.

Oct. 10, 2013 Office Action issued in connection with U.S. Appl. No. 13/560,872.

Aug. 15, 2013 Office Action issued in connection with U.S. Appl. No. 13/560,851.

Nov. 15, 2013 Response to Aug. 15, 2013 Office Action issued in connection with U.S. Appl. No. 13/560,851.

Comi et al. (2010) "Oral laquinimod in patients with relapsing-remitting multiple sclerosis . . ." Mult. Scler. vol. 16, pp. 1360-1366.

Reagan-Shaw et al. (2007) "Dose translation from animal to human sturdies revisited" FASEB J 22:659-661.

"Guidance for Industry—Estimating the Maximum Safe Starting Dose in Initial Clinical Trials . . ."U.S. Department of Health and Human Services, Jul. 2005.

Runstrom et al. (2006) "Inhibition of the development of chronic experimental autoimmune encephalomyelitis by laquinimod . . ." J. of Neuroimmunology, vol. 173, pp. 69-78.

Andersson Bjorn (2006) "Active Biotech: Market misjudges Laquinimod" Redeye update Sep. 27, 2006.

Ytterberg et al. (2007) "Combination therapy with interferon-beta and glatiramer acetate in multiple sclerosis", Acta Neurol Scand., 116(2):96-99.

Conway et al. (2010) "Combination Therapy in Multiple Sclerosis", Lancet Neurology, 9(3):299-308, Mar. 2010.

t'Hart et al. (2004) "Modeling of Multiple Sclerosis: lessons learned in a non-human primate", The Lancet Neurology, 3(10):588-597, Oct. 2004.

Wekerle et al. (2006) "Animal models of multiple sclerosis", Drug Discovery Today: Disease Models, 3(4):359-367.

Velez, L. et al. "Opisthotonic Posturing With Neuromuscular Irritability Attributable to 4-Aminopyridine Ingestion . . .", vol. 111, No. 1, Jan. 1, 2003, p. 83.

Palmer, A. "Pharmacotherapeutic-Options-for-the-Treatment-of-Multiple-Sclerosis" Clinical Medicine Insights: Therapeutics, Apr. 2012, vol. 4, pp. 145-168.

\* cited by examiner

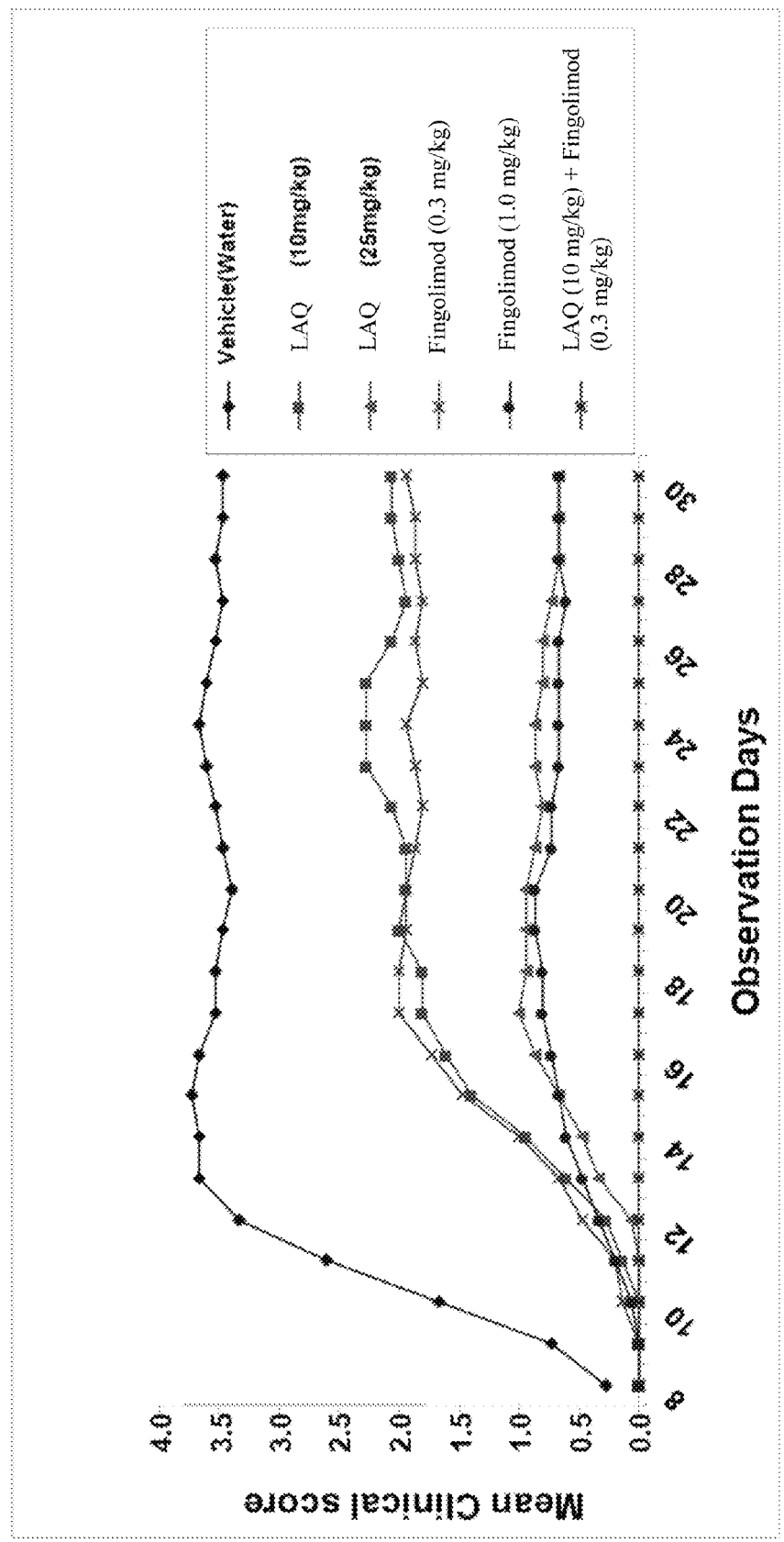

TREATMENT OF MULTIPLE SCLEROSIS WITH COMBINATION OF LAQUINIMOD AND FINGOLIMOD

This application claims benefit of U.S. Provisional Application No. 61/546,102, filed Oct. 12, 2011, the entire content of which is hereby incorporated by reference herein.

Throughout this application, various publications are referred to by first author and year of publication. Full citations for these publications are presented in a References section immediately before the claims. Disclosures of the documents and publications referred to herein are hereby incorporated in their entireties by reference into this application.

BACKGROUND

Multiple Sclerosis (MS) is a neurological disease affecting more than 1 million people worldwide. It is the most common cause of neurological disability in young and middle-aged adults and has a major physical, psychological, social and financial impact on subjects and their families, friends and bodies responsible for health care (EMEA Guideline, 2006).

It is generally assumed that MS is mediated by some kind of autoimmune process possibly triggered by infection and superimposed upon a genetic predisposition. It is a chronic inflammatory condition that damages the myelin of the Central Nervous System (CNS). The pathogenesis of MS is characterized by the infiltration of autoreactive T-cells from the circulation directed against myelin antigens into the CNS (Bjartmar, 2002). In addition to the inflammatory phase in MS, axonal loss occurs early in the course of the disease and can be extensive over time, leading to the subsequent development of progressive, permanent, neurologic impairment and, frequently, severe disability (Neuhaus, 2003). Symptoms associated with the disease include fatigue, spasticity, ataxia, weakness, bladder and bowel disturbances, sexual dysfunction, pain, tremor, paroxysmal manifestations, visual impairment, psychological problems and cognitive dysfunction (EMEA Guideline, 2006).

MS disease activity can be monitored by cranial scans, including magnetic resonance imaging (MRI) of the brain, accumulation of disability, as well as rate and severity of relapses. The diagnosis of clinically definite MS as determined by the Poser criteria (Poser, 1983) requires at least two neurological events suggesting demyelination in the CNS separated in time and in location. A clinically isolated syndrome (CIS) is a single monosymptomatic attack suggestive of MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesion go on to develop MS, while approximately 20 percent have a self-limited process (Brex, 2002; Frohman, 2003). Various MS disease stages and/or types are described in Multiple Sclerosis Therapeutics (Duntiz, 1999). Among them, relapsing-remitting multiple sclerosis (RRMS) is the most common form at the time of initial diagnosis. Many subjects with RRMS have an initial relapsing-remitting course for 5-15 years, which then advances into the secondary progressive MS (SPMS) disease course. Relapses result from inflammation and demyelination, whereas restoration of nerve conduction and remission is accompanied by resolution of inflammation, redistribution of sodium channels on demyelinated axons and remyelination (Neuhaus, 2003; Noseworthy, 2000).

In April 2001, an international panel in association with the National MS Society of America recommended diagnostic criteria for multiple sclerosis. These criteria became known as the McDonald Criteria: The McDonald Criteria make use of MRI techniques and are intended to replace the Poser Criteria and the older Schumacher Criteria (McDonald, 2001). The McDonald Criteria was revised in March 2005 by an international panel (Polman, 2005) and updated again in 2010 (Polman, 2011).

Intervention with disease-modifying therapy at relapsing stages of MS is suggested to reduce and/or prevent accumulating neurodegeneration (Hohlfeld, 2000; De Stefano, 1999). There are currently a number of disease-modifying medications approved for use in relapsing MS (RMS), which includes RRMS and SPMS (The Disease Modifying Drug Brochure, 2006). These include interferon beta 1-a (Avonex® and Rebif®), interferon beta 1-b (Betaseron®), glatiramer acetate (Copaxone®), mitoxantrone (Novantrone®), natalizumab (Tysabri®) and Fingolimod (Gilenya®). Most of them are believed to act as immunomodulators. Mitoxantrone and natalizumab are believed to act as immunesuppressants. However, the mechanisms of action of each have been only partly elucidated. Immunosuppressants or cytotoxic agents are used in some subjects after failure of conventional therapies. However, the relationship between changes of the immune response induced by these agents and the clinical efficacy in MS is far from settled (EMEA Guideline, 2006).

Other therapeutic approaches include symptomatic treatment which refers to all therapies applied to improve the symptoms caused by the disease (EMEA Guideline, 2006) and treatment of acute relapses with corticosteroids. While steroids do not affect the course of MS over time, they can reduce the duration and severity of attacks in some subjects.

Fingolimod

Fingolimod (Fingolimod, Gilenya™) is a new class of drugs called sphingosine 1-phosphate (S1P) receptor modulators. These medicines reduce inflammation and may also have a direct beneficial effect on cells in the central nervous system (CNS). Upon administration, fingolimod is phosphorylated by sphingosine kinase to form the active metabolite fingolimod-phosphate-Fingolimod is therefore a prodrug. Fingolimod-phosphate binds the sphingosine 1-phosphate receptors S1PR-1, S1PR3, S1PR4 and S1PR5 with high affinity and thereby blocks the capacity of leukocytes to migrate from lymph nodes into the peripheral blood. These receptors are also known as EDG receptors, and are all members of the rhodospin-like GPCR family, the largest single historical successful family of drug targets (GPCR SARfari: S1PR-1 (aka. EDG1)). The curative mechanism underlying fingolimod's therapeutic effect is unknown but may involve a reduced migration of lymphocytes into the CNS. The chemical structure of fingolimod was derived from the myriocin (ISP-1) metabolite of the fungus *Isaria sinclairii*. It is a structural analogue of sphingosine and gets phosphorylated by sphingosine kinases in the cell (most importantly sphingosine kinase 2) (Paugh S W 2003; Billich A, 2003; Sanchez, T, 2003). The molecular biology of phospho-fingolimod is thought to lie in its activity at one of the five sphingosine-1-phosphate receptors, S1PR1(H1a T, 2001). It can sequester lymphocytes in lymph nodes, preventing them from moving to the central nervous system for auto-immune responses in multiple sclerosis and was originally proposed as a anti-rejection medication indicated post-transplantation. It has been reported to stimulate the repair process of glial cells and precursor cells after injury (Alejandro Horga, 2008). Fingolimod has also been reported to be a cannabinoid receptor antagonist (Paugh S W, 2006), a cPLA2 inhibitor (Payne S G, 2007) and a ceramide synthase inhibitor (Berdyshev E V, 2009).

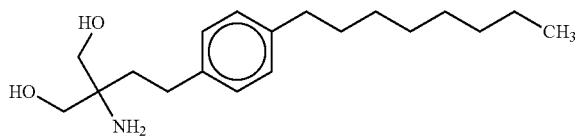

IUPAC:
2-amino-2-[2-(4-octylphenyl)ethyl]propane-1,3-diol

The approved medication Gilenya is an oral capsule containing 0.56 mg of the hydrochloride salt of fingolimod which is equivalent to 0.5 mg of fingolimod.

Laquinimod

Laquinimod is a novel synthetic compound with high oral bioavailability which has been suggested as an oral formulation for the treatment of Multiple Sclerosis (MS) (Polman, 2005; Sandberg-Wollheim, 2005; Comi et al 2008). Laquinimod and its sodium salt form are described, for example, in U.S. Pat. No. 6,077,851. The mechanism of action of laquinimod is not fully understood.

Animal studies show it causes a Th1 (T helper 1 cell, produces pro-inflammatory cytokines) to Th2 (T helper 2 cell, produces anti-inflammatory cytokines) shift with an anti-inflammatory profile (Yang, 2004; Brück, 2011). Another study demonstrated (mainly via the NFkB pathway) that laquinimod induced suppression of genes related to antigen presentation and corresponding inflammatory pathways (Gurevich, 2010). Other suggested potential mechanisms of action include inhibition of leukocyte migration into the CNS, increase of axonal integrity, modulation of cytokine production, and increase in levels of brain-derived neurotrophic factor (BDNF) (Runström, 2006; Brück, 2011).

Laquinimod showed a favorable safety and tolerability profile in two phase III trials (Results of Phase III BRAVO Trial Reinforce Unique Profile of Laquinimod for Multiple Sclerosis Treatment; Teva Pharma, Active Biotech Post Positive Laquinimod Phase 3 ALLEGRO Results).

Combination Therapy

The administration of two drugs to treat a given condition, such as multiple sclerosis, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999). In one example, combined administration of fingolimod and interferon (IFN) has been experimentally shown to abrogate the clinical effectiveness of either therapy. (Brod 2000) In another experiment, it was reported that the addition of prednisone in combination therapy with IFN-β antagonized its up-regulator effect. Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug. In one example, the combination of natalizumab and interferon β-1a was observed to increase the risk of unanticipated side effects. (Vollmer, 2008; Rudick 2006; Kleinschmidt-DeMasters, 2005; Langer-Gould 2005)

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry, 1999).

Therefore, the state of the art at the time of filing is that the effects of combination therapy of two drugs, in particular laquinimod and fingolimod, cannot be predicted until the results of a combination study are available.

BRIEF DESCRIPTION OF THE DRAWINGS

FIG. 1 is a graphical representation of the experimental results from Example 1. The graph shows the clinical score for the EAE rodents in each group (on the y-axis) against the days after induction of the disease (on the x-axis).

SUMMARY OF THE INVENTION

This invention provides a method of treating a subject afflicted with multiple sclerosis or presenting a clinically isolated syndrome comprising periodically administering to the subject an amount of laquinimod, and an amount of fingolimod, wherein the amounts when taken together are effective to treat the subject.

This invention also provides a method of treating a human patient afflicted with multiple sclerosis or presenting a clinically isolated syndrome comprising periodically administering to the patient an amount of laquinimod and an amount of fingolimod, wherein the amounts when taken together is more effective to treat the human patient than when each agent is administered alone.

This invention also provides a method of treating a human patient afflicted with an immune disease, comprising periodically administering to the patient an amount of laquinimod and an amount of fingolimod, wherein the amounts when taken together are effective to treat the human patient, and wherein the immune disease is an autoimmune disease, an arthritic condition, a demyelinating disease, an inflammatory disease, multiple sclerosis, relapsing-remitting multiple sclerosis, diabetes mellitus, psoriasis, rheumatoid arthritis, inflammatory bowel disease, Crohn's disease, or systemic lupus erythematosus.

This invention also provides a package comprising: a) a first pharmaceutical composition comprising an amount of laquinimod and a pharmaceutically acceptable carrier; b) a second pharmaceutical composition comprising an amount of fingolimod and a pharmaceutically acceptable carrier; and c) instructions for use of the first and second pharmaceutical compositions together to treat a subject afflicted with multiple sclerosis or presenting a clinically isolated syndrome.

This invention also provides laquinimod for use as an add-on therapy or in combination with fingolimod in treating a subject afflicted with multiple sclerosis or presenting a clinically isolated syndrome.

This invention also provides a pharmaceutical composition comprising an amount of laquinimod and an amount of fingolimod for use in treating a subject afflicted with multiple sclerosis or presenting a clinically isolated syndrome, wherein the laquinimod and the fingolimod are administered simultaneously, contemporaneously or concomitantly.

This invention also provides a pharmaceutical composition comprising an amount of laquinimod and an amount of fingolimod for use in treating a human patient afflicted with an immune disease, wherein the laquinimod and the fingolimod are administered simultaneously, contemporaneously, or concomitantly and wherein the immune disease is an autoimmune disease, an arthritic condition, a demyelinating disease, an inflammatory disease, multiple sclerosis, relapsing-remitting multiple sclerosis, diabetes mellitus, psoriasis, rheumatoid arthritis, inflammatory bowel disease, Crohn's disease, or systemic lupus erythematosus.

This invention also provides a pharmaceutical composition comprising an amount of laquinimod and an amount of fingolimod.

This invention also provides use of an amount of laquinimod and an amount of fingolimod in the preparation of a combination for treating a subject afflicted with multiple sclerosis or presenting a clinically isolated syndrome wherein the laquinimod and the fingolimod are administered simultaneously, contemporaneously or concomitantly.

This invention also provides pharmaceutical composition comprising an amount of laquinimod for use in treating a subject afflicted with multiple sclerosis or presenting a clinically isolated syndrome as an add-on therapy or in combination with fingolimod by periodically administering the pharmaceutical composition and the fingolimod to the subject.

This invention also provides a pharmaceutical composition comprising an amount of fingolimod for use in treating a subject afflicted with multiple sclerosis or presenting a clinically isolated syndrome as an add-on therapy or in combination with laquinimod by periodically administering the pharmaceutical composition and the laquinimod to the subject.

This invention also provides a therapeutic package for dispensing to, or for use in dispensing to, a subject afflicted with multiple sclerosis or presenting a clinically isolated syndrome, which comprises: a) one or more unit doses, each such unit dose comprising: i) an amount of laquinimod and ii) an amount of fingolimod wherein the respective amounts of said laquinimod and said fingolimod in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject.

This invention further provides a pharmaceutical composition in unit dosage form, useful in treating a subject afflicted with multiple sclerosis or presenting a clinically isolated syndrome, which comprises: a) an amount of laquinimod; b) an amount of fingolimod, wherein the respective amounts of said laquinimod and said fingolimod in said composition are effective, upon concomitant administration to said subject of one or more of said unit dosage forms of said composition, to treat the subject.

DETAILED DESCRIPTION OF THE INVENTION

This invention provides a method of treating a subject afflicted with multiple sclerosis or presenting a clinically isolated syndrome comprising periodically administering to the subject an amount of laquinimod and an amount of fingolimod, wherein the amounts when taken together are effective to treat the subject.

This invention also provides a method of treating a human patient afflicted with multiple sclerosis or presenting a clinically isolated syndrome comprising periodically administering to the patient an amount of laquinimod and an amount of fingolimod, wherein the amounts when taken together is more effective to treat the human patient than when each agent is administered alone.

This invention also provides a method of treating a human patient afflicted with an immune disease, comprising periodically administering to the patient an amount of laquinimod and an amount of fingolimod, wherein the amounts when taken together are effective to treat the human patient, and wherein the immune disease is an autoimmune disease, an arthritic condition, a demyelinating disease, an inflammatory disease, multiple sclerosis, relapsing-remitting multiple sclerosis, diabetes mellitus, psoriasis, rheumatoid arthritis, inflammatory bowel disease, Crohn's disease, or systemic lupus erythematosus.

In an embodiment, the amount of laquinimod and the amount of fingolimod when administered together is more effective to treat the subject than when each agent at the same amount is administered alone.

In one embodiment, the multiple sclerosis is relapsing multiple sclerosis. In another embodiment, the relapsing multiple sclerosis is relapsing-remitting multiple sclerosis.

In an embodiment, the amount of laquinimod and the amount of fingolimod when taken together is effective to reduce a symptom of multiple sclerosis in the subject. In one embodiment, the symptom is a MRI-monitored multiple sclerosis disease activity, relapse rate, accumulation of physical disability, frequency of relapses, decreased time to confirmed disease progression, decreased time to confirmed relapse, frequency of clinical exacerbation, brain atrophy, neuronal dysfunction, neuronal injury, neuronal degeneration, neuronal apoptosis, risk for confirmed progression, deterioration of visual function, fatigue, impaired mobility, cognitive impairment, reduction of brain volume, abnormalities observed in whole Brain MTR histogram, deterioration in general health status, functional status, quality of life, and/or symptom severity on work.

In one embodiment, the amount of laquinimod and the amount of fingolimod when taken together is effective to decrease or inhibit reduction of brain volume. In another embodiment, brain volume is measured by percent brain volume change (PBVC).

In one embodiment, the amount of laquinimod and the amount of fingolimod when taken together is effective to increase time to confirmed disease progression. In another embodiment, time to confirmed disease progression is increased by 20-60%. In another embodiment, time to confirmed disease progression is increased by at least 50%.

In one embodiment, the amount of laquinimod and the amount of fingolimod when taken together is effective to decrease abnormalities observed in whole Brain MTR histogram. In another embodiment, the accumulation of physical disability is measured by Kurtzke Expanded Disability Status Scale (EDSS) score. In another embodiment, the accumulation of physical disability is assessed by the time to confirmed disease progression as measured by Kurtzke Expanded Disability Status Scale (EDSS) score.

In one embodiment, the subject had an EDSS score of 0-5.5 at baseline. In another embodiment, the subject had an EDSS score of 1.5-4.5 at baseline. In another embodiment, the subject had an EDSS score of 5.5 or greater at baseline. In another embodiment, confirmed disease progression is a 1 point increase of the EDSS score. In another embodiment, confirmed disease progression is a 0.5 point increase of the EDSS score.

In one embodiment, impaired mobility is assessed by the Timed-25 Foot Walk test. In another embodiment, impaired mobility is assessed by the 12-Item Multiple Sclerosis Walking Scale (MSWS-12) self-report questionnaire. In another embodiment, impaired mobility is assessed by the Ambulation Index (AI). In another embodiment, impaired mobility is assessed by the Six-Minute Walk (6MW) Test. In another embodiment, impaired mobility is assessed by the Lower Extremity Manual Muscle Test (LEMMT) Test.

In an embodiment, the amount of laquinimod and the amount of fingolimod when taken together is effective to reduce cognitive impairment. In another embodiment, cognitive impairment is assessed by the Symbol Digit Modalities Test (SDMT) score.

In an embodiment, general health status is assessed by the EuroQoL (EQ5D) questionnaire, Subject Global Impression (SGI) or Clinician Global Impression of Change (CGIC). In another embodiment, functional status is measured by the subject's Short-Form General Health survey (SF-36) Subject Reported Questionnaire score. In another embodiment, quality of life is assessed by SF-36, EQ5D, Subject Global Impression (SGI) or Clinician Global Impression of Change (CGIC). In another embodiment, the subject's SF-36 mental component summary score (MSC) is improved. In another embodiment, the subject's SF-36 physical component summary sore (PSC) is improved. In another embodiment, fatigue is assessed by the EQ5D, the subject's Modified Fatigue Impact Scale (MFIS) score or the French valid versions of the Fatigue Impact Scale (EMIF-SEP) score. In another embodiment, symptom severity on work is measured by the work productivity and activities impairment General Health (WPAI-GH) questionnaire.

In one embodiment, laquinimod is laquinimod sodium. In another embodiment, fingolimod is fingolimod hydrochloride.

In one embodiment, the laquinimod and/or the fingolimod is administered via oral administration. In another embodiment, the laquinimod and/or the fingolimod is administered daily. In another embodiment, the laquinimod and/or the fingolimod is administered more often than once daily. In another embodiment, the laquinimod and/or the fingolimod is administered less often than once daily.

In one embodiment, the amount laquinimod administered is less than 0.6 mg/day. In another embodiment, the amount laquinimod administered is 0.1-40.0 mg/day. In another embodiment, the amount laquinimod administered is 0.1-2.5 mg/day. In another embodiment, the amount laquinimod administered is 0.25-2.0 mg/day. In another embodiment, the amount laquinimod administered is 0.5-1.2 mg/day. In another embodiment, the amount laquinimod administered is 0.25 mg/day. In another embodiment, the amount laquinimod administered is 0.3 mg/day. In another embodiment, the amount laquinimod administered is 0.5 mg/day. In another embodiment, the amount laquinimod administered is 0.6 mg/day. In another embodiment, the amount laquinimod administered is 1.0 mg/day. In another embodiment, the amount laquinimod administered is 1.2 mg/day. In another embodiment, the amount laquinimod administered is 1.5 mg/day. In another embodiment, the amount laquinimod administered is 2.0 mg/day.

In one embodiment, the amount of fingolimod administered is less than 0.5 mg/day. In another embodiment, the amount of fingolimod administered is 0.01-2.5 mg/day. In another embodiment, the amount of fingolimod administered is 2.5 mg/day. In another embodiment, the amount of fingolimod administered is 0.01-1 mg/day. In another embodiment, the amount of fingolimod administered is 0.1 mg/day. In another embodiment, the amount of fingolimod administered is 0.25 mg/day. In another embodiment, the amount of fingolimod administered is 0.5 mg/day.

In one embodiment, the amount of laquinimod and the amount of fingolimod when taken together is effective to alleviate a symptom of multiple sclerosis in the subject. In another embodiment, the symptom is a MRI-monitored multiple sclerosis disease activity, relapse rate, accumulation of physical disability, frequency of relapses, frequency of clinical exacerbation, brain atrophy, risk for confirmed progression, or time to confirmed disease progression.

In one embodiment, a loading dose of an amount different form the intended dose is administered for a period of time at the start of the periodic administration. In another embodiment, the loading dose is double the amount of the intended dose.

In one embodiment, the subject is receiving laquinimod therapy prior to initiating fingolimod therapy. In another embodiment, the administration of laquinimod substantially precedes the administration of fingolimod. In one embodiment, the subject is receiving fingolimod therapy prior to initiating laquinimod therapy. In another embodiment, the administration of fingolimod substantially precedes the administration of laquinimod. In another embodiment, the subject is receiving fingolimod therapy for at least 24 weeks prior to initiating laquinimod therapy. In another embodiment, the subject is receiving fingolimod therapy for at least 28 weeks prior to initiating laquinimod therapy. In another embodiment, the subject is receiving fingolimod therapy for at least 48 weeks prior to initiating laquinimod therapy. In yet another embodiment, the subject is receiving fingolimod therapy for at least 52 weeks prior to initiating laquinimod therapy.

In one embodiment, the method further comprises administration of nonsteroidal anti-inflammatory drugs (NSAIDs), salicylates, slow-acting drugs, gold compounds, hydroxychloroquine, sulfasalazine, combinations of slow-acting drugs, corticosteroids, cytotoxic drugs, immunosuppressive drugs and/or antibodies.

In one embodiment, the periodic administration of laquinimod o and fingolimod continues for at least 3 days. In another embodiment, the periodic administration of laquinimod and fingolimod continues for more than 30 days. In another embodiment, the periodic administration of laquinimod and fingolimod continues for more than 42 days. In another embodiment, the periodic administration of laquinimod and fingolimod continues for 8 weeks or more. In another embodiment, the periodic administration of laquinimod and fingolimod continues for at least 12 weeks. In another embodiment, the periodic administration of laquinimod and fingolimod continues for at least 24 weeks. In another embodiment, the periodic administration of laquinimod and fingolimod continues for more than 24 weeks. In yet another embodiment, the periodic administration of laquinimod and fingolimod continues for 6 months or more.

In one embodiment, the administration of laquinimod and fingolimod inhibits a symptom of relapsing multiple sclerosis by at least 20%. In another embodiment, the administration of laquinimod and fingolimod inhibits a symptom of relapsing multiple sclerosis by at least 30%. In another embodiment, the administration of laquinimod and fingolimod inhibits a symptom of relapsing multiple sclerosis by at least 50%. In another embodiment, the administration of laquinimod and fingolimod or inhibits a symptom of relapsing multiple sclerosis by at least 70%. In another embodiment, the administration of laquinimod and fingolimod inhibits a symptom of relapsing multiple sclerosis by more than 100%. In another embodiment, the administration of laquinimod and fingolimod inhibits a symptom of relapsing multiple sclerosis by more than 300%. In another embodiment, the administration of laquinimod and fingolimod inhibits a symptom of relapsing multiple sclerosis by more than 1000%.

In one embodiment, each of the amount of laquinimod when taken alone, and the amount of fingolimod or when taken alone is effective to treat the subject. In another embodiment, either the amount of laquinimod when taken alone, the amount of fingolimod or when taken alone, or each such amount when taken alone is not effective to treat the subject. In yet another embodiment, the subject is a human patient.

This invention also provides a package comprising: a) a first pharmaceutical composition comprising an amount of laquinimod and a pharmaceutically acceptable carrier; b) a second pharmaceutical composition comprising an amount of fingolimod and a pharmaceutically acceptable carrier; and c) instructions for use of the first and second pharmaceutical compositions together to treat a subject afflicted with multiple sclerosis or presenting a clinically isolated syndrome.

In one embodiment, the first pharmaceutical composition, the second pharmaceutical composition, or both the first and the second pharmaceutical composition are in an aerosol, an inhalable powder, an injectable a liquid, a solid, a capsule or a tablet form. In one embodiment, the first pharmaceutical composition, the second pharmaceutical composition, or both the first and the second pharmaceutical composition are in liquid form. In another embodiment, the first pharmaceutical composition, the second pharmaceutical composition, or both the first and the second pharmaceutical composition are in solid form. In another embodiment, the first pharmaceutical composition, the second pharmaceutical composition, or both the first and the second pharmaceutical composition are in capsule form. In another embodiment, the first pharmaceutical composition, the second pharmaceutical composition, or both the first and the second pharmaceutical composition are in tablet form. In another embodiment, the tablets are coated with a coating which inhibits oxygen from contacting the core. In another embodiment, the coating comprises a cellulosic polymer, a detackifier, a gloss enhancer, or pigment.

In one embodiment, the first pharmaceutical composition further comprises mannitol. In another embodiment, the first pharmaceutical composition further comprises an alkalinizing agent. In another embodiment, the alkalinizing agent is meglumine.

In one embodiment, the first pharmaceutical composition further comprises an oxidation reducing agent. In another embodiment, the first pharmaceutical composition is stable and free of an alkalinizing agent or an oxidation reducing agent. In another embodiment, the first pharmaceutical composition is free of an alkalinizing agent and free of an oxidation reducing agent. In another embodiment, the first pharmaceutical composition is stable and free of disintegrant.

In one embodiment, the first pharmaceutical composition further comprises a lubricant. In another embodiment, the lubricant is present in the composition as solid particles. In another embodiment, the lubricant is sodium stearyl fumarate or magnesium stearate.

In one embodiment, the first pharmaceutical composition further comprises a filler. In another embodiment, the filler is present in the composition as solid particles. In another embodiment, the filler is lactose, lactose monohydrate, starch, isomalt, mannitol, sodium starch glycolate, sorbitol, lactose spray dried, lactose anhydrouse, or a combination thereof. In yet another embodiment, the filler is mannitol or lactose monohydrate.

In an embodiment, the package further comprises a desiccant. In another embodiment, the desiccant is silica gel.

In one embodiment, the first pharmaceutical composition is stable and has a moisture content of no more than 4%. In another embodiment, laquinimod is present in the composition as solid particles. In another embodiment, the package is a sealed packaging having a moisture permeability of not more than 15 mg/day per liter. In another embodiment, the sealed package is a blister pack in which the maximum moisture permeability is no more than 0.005 mg/day. In another embodiment, the sealed package is a bottle. In another embodiment, the bottle is closed with a heat induction liner. In another embodiment, the sealed package comprises an HDPE bottle. In another embodiment, the sealed package comprises an oxygen absorbing agent. In yet another embodiment, the oxygen absorbing agent is iron.

In an embodiment of the present invention, the amount of laquinimod in the first composition is less than 0.6 mg. In another embodiment, the amount of laquinimod in the first composition is 0.1-40.0 mg. In another embodiment, the amount of laquinimod in the first composition is 0.1-2.5 mg. In another embodiment, the amount of laquinimod in the first composition is 0.25-2.0 mg. In another embodiment, the amount of laquinimod in the first composition is 0.5-1.2 mg. In another embodiment, the amount of laquinimod in the first composition is 0.25 mg. In another embodiment, the amount of laquinimod in the first composition is 0.3 mg. In another embodiment, the amount of laquinimod in the first composition is 0.5 mg. In another embodiment, the amount of laquinimod in the first composition is 0.6 mg. In another embodiment, the amount of laquinimod in the first composition is 1.0 mg. In another embodiment, the amount of laquinimod in the first composition is 1.2 mg. In another embodiment, the amount of laquinimod in the first composition is 1.5 mg. In another embodiment, the amount of laquinimod in the first composition is 2.0 mg.

In an embodiment of the present invention, the amount of fingolimod in the second composition is less than 0.5 mg. In another embodiment of the present invention, the amount of fingolimod in the second composition is 0.01-2.5 mg. In another embodiment, the amount of fingolimod in the second composition is 2.5 mg. In another embodiment, the amount of fingolimod in the second composition is 0.01-1 mg. In another embodiment, the amount of fingolimod in the second composition is 0.1 mg. In another embodiment, the amount of fingolimod in the second composition is 0.25 mg. In another embodiment, the amount of fingolimod in the second composition is 0.5 mg.

This invention also provides laquinimod for use as an add-on therapy or in combination with fingolimod or in treating a subject afflicted with multiple sclerosis or presenting a clinically isolated syndrome.

This invention also provides a pharmaceutical composition comprising an amount of laquinimod and an amount of fingolimod for use in treating a subject afflicted with multiple sclerosis or presenting a clinically isolated syndrome, wherein the laquinimod and the fingolimod f are administered simultaneously, contemporaneously or concomitantly.

This invention also provides a pharmaceutical composition comprising an amount of laquinimod and an amount of fingolimod for use in treating a human patient afflicted with an immune disease, wherein the laquinimod and the fingolimod are administered simultaneously, contemporaneously, or concomitantly and wherein the immune disease is an autoimmune disease, an arthritic condition, a demyelinating disease, an inflammatory disease, multiple sclerosis, relapsing-remitting multiple sclerosis, diabetes mellitus, psoriasis, rheumatoid arthritis, inflammatory bowel disease, Crohn's disease, or systemic lupus erythematosus.

This invention also provides a pharmaceutical composition comprising an amount of laquinimod and an amount of fingolimod.

In one embodiment, laquinimod is laquinimod sodium. In another embodiment, fingolimod is fingolimod hydrochloride.

In one embodiment, the composition is in an aerosol, an inhalable powder, an injectable, a liquid, a solid, a capsule or a tablet form. In another embodiment, the composition is in liquid form. In another embodiment, the composition is in solid form. In another embodiment, the composition is in capsule form. In another embodiment, the composition is in tablet form.

In one embodiment, the tablets are coated with a coating which inhibits oxygen from contacting the core. In another embodiment, the coating comprises a cellulosic polymer, a detackifier, a gloss enhancer, or pigment.

In one embodiment, the pharmaceutical composition further comprises mannitol. In another embodiment, the pharmaceutical composition further comprises an alkalinizing agent. In another embodiment, the alkalinizing agent is meglumine. In an embodiment, the pharmaceutical composition comprises an oxidation reducing agent.

In an embodiment the pharmaceutical composition is free of an alkalinizing agent or an oxidation reducing agent. In another embodiment, the pharmaceutical composition is free of an alkalinizing agent and free of an oxidation reducing agent.

In one embodiment, the pharmaceutical composition is stable and free of disintegrant. In another embodiment, the pharmaceutical composition further comprises a lubricant. In another embodiment, the lubricant is present in the composition as solid particles. In another embodiment, the lubricant is sodium stearyl fumarate or magnesium stearate.

In an embodiment, the pharmaceutical composition further comprises a filler. In another embodiment, the filler is present in the composition as solid particles. In another embodiment, the filler is lactose, lactose monohydrate, starch, isomalt, mannitol, sodium starch glycolate, sorbitol, lactose spray dried, lactose anhydrouse, or a combination thereof. In another embodiment, the filler is mannitol or lactose monohydrate.

In one embodiment, the amount of laquinimod in the composition is less than 0.6 mg. In another embodiment, the amount of laquinimod in the composition is 0.1-40.0 mg. In another embodiment, the amount of laquinimod in the composition is 0.1-2.5 mg. In another embodiment, the amount of laquinimod in the composition is 0.25-2.0 mg. In another embodiment, the amount of laquinimod in the composition is 0.1-2.5 mg. In another embodiment, the amount of laquinimod in the composition is 0.25 mg. In another embodiment, the amount of laquinimod in the composition is 0.3 mg. In another embodiment, the amount of laquinimod in the composition is 0.5 mg. In another embodiment, the amount of laquinimod in the composition is 0.6 mg. In another embodiment, the amount of laquinimod in the composition is 1.0 mg. In another embodiment, the amount of laquinimod in the composition is 1.2 mg. In another embodiment, the amount of laquinimod in the composition is 1.5 mg. In another embodiment, the amount of laquinimod in the composition is 2.0 mg.

In one embodiment, the amount of fingolimod in the composition is less than 0.5 mg. In another embodiment, the amount of fingolimod in the composition is 0.01-2.5 mg. In another embodiment, the amount of fingolimod in the composition is 2.5 mg. In another embodiment, the amount of fingolimod in the composition is 0.01-1 mg. In another embodiment, the amount of fingolimod in the composition is 0.1 mg. In another embodiment, the amount of fingolimod in the composition is 0.25 mg. In another embodiment, the amount of fingolimod in the composition is 0.5 mg.

This invention also provides use of an amount of laquinimod and an amount of fingolimod in the preparation of a combination for treating a subject afflicted with multiple sclerosis or presenting a clinically isolated syndrome wherein the laquinimod or pharmaceutically acceptable salt thereof and the fingolimod or pharmaceutically acceptable salt thereof are administered simultaneously, contemporaneously or concomitantly.

In one embodiment, the multiple sclerosis is relapsing multiple sclerosis. In another embodiment, the relapsing multiple sclerosis is relapsing-remitting multiple sclerosis.

This invention also provides a pharmaceutical composition comprising an amount of laquinimod for use in treating a subject afflicted with multiple sclerosis or presenting a clinically isolated syndrome as an add-on therapy or in combination with fingolimod by periodically administering the pharmaceutical composition and the fingolimod to the subject.

This invention also provides a pharmaceutical composition comprising an amount of fingolimod for use treating a subject afflicted with multiple sclerosis or presenting a clinically isolated syndrome as an add-on therapy or in combination with laquinimod by periodically administering the pharmaceutical composition and the laquinimod to the subject.

This invention also provides a therapeutic package for dispensing to, or for use in dispensing to, a subject afflicted with multiple sclerosis or presenting a clinically isolated syndrome, which comprises: a) one or more unit doses, each such unit dose comprising: i) an amount of laquinimod and ii) an amount of fingolimod wherein the respective amounts of said laquinimod and said fingolimod in said unit dose are effective, upon concomitant administration to said subject, to treat the subject, and b) a finished pharmaceutical container therefor, said container containing said unit dose or unit doses, said container further containing or comprising labeling directing the use of said package in the treatment of said subject. In an embodiment, the respective amounts of said laquinimod and said fingolimod in said unit dose when taken together is more effective to treat the subject than when compared to the administration of said laquinimod in the absence of said fingolimod or the administration of said fingolimod in the absence of said laquinimod.

This invention further provides a pharmaceutical composition in unit dosage form, useful in treating a subject afflicted with multiple sclerosis or presenting a clinically isolated syndrome, which comprises: a) an amount of laquinimod; b) an amount of fingolimod, wherein the respective amounts of said laquinimod and said fingolimod in said composition are effective, upon concomitant administration to said subject of one or more of said unit dosage forms of said composition, to treat the subject. In an embodiment, the respective amounts of said laquinimod and said fingolimod in said unit dose when taken together is more effective to treat the subject than when compared to the administration of said laquinimod in the absence of said fingolimod or the administration of said fingolimod in the absence of said laquinimod.

For the foregoing embodiments, each embodiment disclosed herein is contemplated as being applicable to each of the other disclosed embodiments.

Fingolimod

Fingolimod mixtures, compositions, the process for the manufacture thereof, the use thereof for treatment of various conditions, and the corresponding dosages and regimens are described in, e.g., U.S. Patent Application Publication Nos. 2012-0184617, 2009-0176744, 2009-0082347, and 2011-0152380, U.S. Pat. No. 5,719,176, and Pelletier and Hafler (2012) "Fingolimod for Multiple Sclerosis" New England Journal of Medicine, 366(4):339-347, each of which is hereby incorporated by reference in its entireties into this application.

Laquinimod

Laquinimod mixtures, compositions, and the process for the manufacture thereof are described in, e.g., U.S. Pat. No. 6,077,851, U.S. Pat. No. 7,884,208, U.S. Pat. No. 7,989,473, U.S. Pat. No. 8,178,127, U.S. Application Publication No. 2010-0055072, U.S. Application Publication No. 2012-0010238, and U.S. Application Publication No. 2012-0010239, each of which is hereby incorporated by reference in its entireties into this application.

Use of laquinimod for treatment of various conditions, and the corresponding dosages and regimens, are described in U.S. Pat. No. 6,077,851 (multiple sclerosis, insulin-dependent diabetes mellitus, systemic lupus erythematosus, rheumatoid arthritis, inflammatory bowel disease, psoriasis, inflammatory respiratory disorder, atherosclerosis, stroke, and Alzheimer's disease), U.S. Application Publication No. 2011-0027219 (Crohn's disease), U.S. Application Publication No. 2010-0322900 (Relapsing-remitting multiple sclerosis), U.S. Application Publication No. 2011-0034508 (brain-derived neurotrophic factor (BDNF)-related diseases), U.S. Application Publication No. 2011-0218179 (active lupus nephritis), U.S. Application Publication No. 2011-0218203 (rheumatoid arthritis), U.S. Application Publication No. 2011-0217295 (active lupus arthritis), and U.S. Application Publication No. 2012-0142730 (reducing fatigue, improving quality of life, and providing neuroprotection in MS patients), each of which is hereby incorporated by reference in its entireties into this application.

A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Pat. No. 7,589,208 and PCT International Application Publication No. WO 2005/074899, which are hereby incorporated by reference into this application.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit can be in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Specific examples of the techniques, pharmaceutically acceptable carriers and excipients that may be used to formulate oral dosage forms of the present invention are described, e.g., in U.S. Pat. No. 7,589,208, PCT International Application Publication Nos. WO 2005/074899, WO 2007/047863, and 2007/146248.

General techniques and compositions for making dosage forms useful in the present invention are described in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds); Modern Pharmaceutics Drugs and the Pharmaceutical Sciences, Vol. 40 (Gilbert S. Banker, Christopher T. Rhodes, Eds). These references in their entireties are hereby incorporated by reference into this application.

Disclosed is a method for treating a subject, e.g., human patient, afflicted with relapsing multiple sclerosis or presenting a CIS using laquinimod with fingolimod which provides a more efficacious treatment than each agent alone. The use of laquinimod for relapsing multiple sclerosis had been previously suggested in, e.g., U.S. Pat. No. 6,077,851. However, the inventors have surprisingly found that the combination of laquinimod and fingolimod is particularly effective for the treatment of a subject afflicted with MS or presenting a CIS as compared to each agent alone.

Terms

As used herein, and unless stated otherwise, each of the following terms shall have the definition set forth below.

As used herein, "laquinimod" means laquinimod acid or a pharmaceutically acceptable salt thereof.

As used herein, "fingolimod" means fingolimod acid or a pharmaceutically acceptable salt thereof.

As used herein, an "amount" or "dose" of laquinimod or fingolimod as measured in milligrams refers to the milligrams of laquinimod or fingolimod acid present in a preparation, regardless of the form of the preparation. A "dose of 0.6 mg laquinimod" means the amount of laquinimod acid in a preparation is 0.6 mg, regardless of the form of the preparation. Thus, when in the form of a salt, e.g. a laquinimod sodium salt, the weight of the salt form necessary to provide a dose of 0.6 mg laquinimod would be greater than 0.6 mg (e.g., 0.64 mg) due to the presence of the additional salt ion. Similarly, when in the form of a salt, e.g. fingolimod hydrochloride, the weight of the salt form necessary to provide a dose of 0.5 mg fingolimod would be greater than 0.5 mg (e.g., 0.56 mg) due to the presence of the additional salt ion.

As used herein, a "unit dose", "unit doses" and "unit dosage form(s)" mean a single drug administration entity/entities.

As used herein, "about" in the context of a numerical value or range means ±10% of the numerical value or range recited or claimed.

As used herein, a composition that is "free" of a chemical entity means that the composition contains, if at all, an amount of the chemical entity which cannot be avoided although the chemical entity is not part of the formulation and was not affirmatively added during any part of the manufacturing process. For example, a composition which is "free" of an alkalizing agent means that the alkalizing agent, if present at all, is a minority component of the composition by weight. Preferably, when a composition is "free" of a component, the composition comprises less than 0.1 wt %, 0.05 wt %, 0.02 wt %, or 0.01 wt % of the component.

As used herein, "alkalizing agent" is used interchangeably with the term "alkaline-reacting component" or "alkaline agent" and refers to any pharmaceutically acceptable excipient which neutralizes protons in, and raises the pH of, the pharmaceutical composition in which it is used.

As used herein, "oxidation reducing agent" refers to a group of chemicals which includes an "antioxidant", a "reduction agent" and a "chelating agent".

As used herein, "antioxidant" refers to a compound selected from the group consisting of tocopherol, methionine, glutathione, tocotrienol, dimethyl glycine, betaine, butylated hydroxyanisole, butylated hydroxytoluene, turmerin, vitamin E, ascorbyl palmitate, tocopherol, deteroxime mesylate, methyl paraben, ethyl paraben, butylated hydroxyanisole, butylated hydroxytoluene, propyl gallate, sodium or potassium metabisulfite, sodium or potassium sulfite, alpha tocopherol or derivatives thereof, sodium ascorbate, disodium edentate, BHA (butylated hydroxyanisole), a pharmaceutically acceptable salt or ester of the mentioned compounds, and mixtures thereof.

The term "antioxidant" as used herein also refers to Flavonoids such as those selected from the group of quercetin, morin, naringenin and hesperetin, taxifolin, afzelin, quercitrin, myricitrin, genistein, apigenin and biochanin A, flavone, flavopiridol, isoflavonoids such as the soy isoflavonoid, genistein, catechins such as the tea catechin epigallocatechin gallate, flavonol, epicatechin, hesperetin, chrysin, diosmin, hesperidin, luteolin, and rutin.

As used herein, "reduction agent" refers to a compound selected from the group consisting of thiol-containing compound, thioglycerol, mercaptoethanol, thioglycol, thiodiglycol, cysteine, thioglucose, dithiothreitol (DTT), dithio-bis-maleimidoethane (DTME), 2,6-di-tert-butyl-4-methylphenol (BHT), sodium dithionite, sodium bisulphite, formamidine sodium metabisulphite, and ammonium bisulphite."

As used herein, "chelating agent" refers to a compound selected from the group consisting of penicillamine, trientine, N,N'-diethyldithiocarbamate (DDC), 2,3,2'-tetraamine (2,3,2'-tet), neocuproine, N,N,N',N'-tetrakis(2-pyridylmethyl)ethylenediamine (TPEN), 1,10-phenanthroline (PHE), tetraethylenepentamine, triethylenetetraamine and tris(2-carboxyethyl)phosphine (TCEP), ferrioxamine, CP94, EDTA, deferoxainine B (DFO) as the methanesulfonate salt (also known as desferrioxanilne B mesylate (DFOM)), desferal from Novartis (previously Ciba-Giegy), and apoferritin.

As used herein, a pharmaceutical composition is "stable" when the composition preserves the physical stability/integrity and/or chemical stability/integrity of the active pharmaceutical ingredient during storage. Furthermore, "stable pharmaceutical composition" is characterized by its level of degradation products not exceeding 5% at 40° C./75% RH after 6 months or 3% at 55° C./75% RH after two weeks, compared to their level in time zero.

As used herein, "combination" means an assemblage of reagents for use in therapy either by simultaneous or contemporaneous administration. Simultaneous administration refers to administration of an admixture (whether a true mixture, a suspension, an emulsion or other physical combination) of the laquinimod and the fingolimod. In this case, the combination may be the admixture or separate containers of the laquinimod and the fingolimod that are combined just prior to administration. Contemporaneous administration refers to the separate administration of the laquinimod and the fingolimod at the same time, or at times sufficiently close together that a synergistic activity relative to the activity of either the laquinimod or the fingolimod alone is observed.

As used herein, "concomitant administration" or administering "concomitantly" means the administration of two agents given in close enough temporal proximately to allow the individual therapeutic effects of each agent to overlap.

As used herein, "add-on" or "add-on therapy" means an assemblage of reagents for use in therapy, wherein the subject receiving the therapy begins a first treatment regimen of one or more reagents prior to beginning a second treatment regimen of one or more different reagents in addition to the first treatment regimen, so that not all of the reagents used in the therapy are started at the same time. For example, adding laquinimod therapy to a patient already receiving fingolimod therapy.

As used herein, "effective" when referring to an amount of laquinimod and/or fingolimod refers to the quantity of laquinimod and/or fingolimod that is sufficient to yield a desired therapeutic response without undue adverse side effects (such as toxicity, irritation, or allergic response) commensurate with a reasonable benefit/risk ratio when used in the manner of this invention.

"Administering to the subject" or "administering to the (human) patient" means the giving of, dispensing of, or application of medicines, drugs, or remedies to a subject/patient to relieve, cure, or reduce the symptoms associated with a condition, e.g., a pathological condition.

"Treating" as used herein encompasses, e.g., inducing inhibition, regression, or stasis of a disease or disorder, e.g., RMS, or alleviating, lessening, suppressing, inhibiting, reducing the severity of, eliminating or substantially eliminating, or ameliorating a symptom of the disease or disorder.

"Treating" as applied to patients presenting CIS can mean delaying the onset of clinically definite multiple sclerosis (CDMS), delaying the progression to CDMS, reducing the risk of conversion to CDMS, or reducing the frequency of relapse in a patient who experienced a first clinical episode consistent with multiple sclerosis and who has a high risk of developing CDMS.

"Inhibition" of disease progression or disease complication in a subject means preventing or reducing the disease progression and/or disease complication in the subject.

A "symptom" associated with RMS includes any clinical or laboratory manifestation associated with RMS and is not limited to what the subject can feel or observe.

As used herein, "a subject afflicted with multiple sclerosis" or "a subject afflicted with relapsing multiple sclerosis" means a subject who has been clinically diagnosed to have multiple sclerosis or relapsing multiple sclerosis (RMS), which includes relapsing-remitting multiple sclerosis (RRMS) and Secondary Progressive multiple sclerosis (SPMS).

As used herein, a subject at "baseline" is as subject prior to administration of laquinimod.

A "patient at risk of developing MS" (i.e. clinically definite MS) as used herein is a patient presenting any of the known risk factors for MS. The known risk factors for MS include any one of a clinically isolated syndrome (CIS), a single attack suggestive of MS without a lesion, the presence of a lesion (in any of the CNS, PNS, or myelin sheath) without a clinical attack, environmental factors (geographical location, climate, diet, toxins, sunlight), genetics (variation of genes encoding HLA-DRB1, IL7R-alpha and IL2R-alpha), and immunological components (viral infection such as by Epstein-Barr virus, high avidity $CD4^+$ T cells, $CD8^+$ T cells, anti-NF-L, anti-CSF 114(Glc)).

"Clinically isolated syndrome (CIS)" as used herein refers to 1) a single clinical attack (used interchangeably herein with "first clinical event" and "first demyelinating event") suggestive of MS, which, for example, presents as an episode of optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning, and 2) at least one lesion suggestive of MS. In a specific example, CIS diagnosis would be based on a single clinical attack and at least 2 lesions suggestive of MS measuring 6 mm or more in diameter.

"Relapse Rate" is the number of confirmed relapses per unit time. "Annualized relapse rate" is the mean value of the number of confirmed relapses of each patient multiplied by 365 and divided by the number of days that patient is on the study drug.

"Expanded Disability Status Scale" or "EDSS" is a rating system that is frequently used for classifying and standardizing the condition of people with multiple sclerosis. The score ranges from 0.0 representing a normal neurological exam to 10.0 representing death due to MS. The score is based upon neurological testing and examination of functional systems (FS), which are areas of the central nervous system which control bodily functions. The functional systems are: Pyramidal (ability to walk), Cerebellar (coordination), Brain stem (speech and swallowing), Sensory (touch and pain), Bowel and bladder functions, Visual, Mental, and Other (includes any other neurological findings due to MS) (Kurtzke J F, 1983).

A "confirmed progression" of EDSS, or "confirmed disease progression" as measured by EDSS score is defined as a 1 point increase from baseline EDSS if baseline EDSS was between 0 and 5.0, or a 0.5 point increase if baseline EDSS was 5.5. In order to be considered a confirmed progression, the change (either 1 point or 0.5 points) must be sustained for at least 3 months. In addition, confirmation of progression cannot be made during a relapse.

"Adverse event" or "AE" means any untoward medical occurrence in a clinical trial subject administered a medicinal product and which does not have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

"Gd-enhancing lesion" refers to lesions that result from a breakdown of the blood-brain barrier, which appear in contrast studies using gandolinium contrast agents. Gandolinium enhancement provides information as to the age of a lesion, as Gd-enhancing lesions typically occur within a six week period of lesion formation.

"Magnetization Transfer Imaging" or "MTI" is based on the magnetization interaction (through dipolar and/or chemical exchange) between bulk water protons and macromolecular protons. By applying an off resonance radio frequency pulse to the macromolecular protons, the saturation of these protons is then transferred to the bulk water protons. The result is a decrease in signal (the net magnetization of visible protons is reduced), depending on the magnitude of MT between tissue macromolecules and bulk water. "MT" or "Magnetization Transfer" refers to the transfer of longitudinal magnetization from the hydrogen nuclei of water that have restricted motion to the hydrogen nuclei of water that moves with many degrees of freedom. With MTI, the presence or absence of macromolecules (e.g. in membranes or brain tissue) can be seen (Mehta, 1996; Grossman, 1994).

"Magnetization Resonance Spectroscopy" or "MRS" is a specialized technique associated with magnetic resonance imaging (MRI). MRS is used to measure the levels of different metabolites in body tissues. The MR signal produces a spectrum of resonances that correspond to different molecular arrangements of the isotope being "excited". This signature is used to diagnose certain metabolic disorders, especially those affecting the brain, (Rosen, 2007) as well as to provide information on tumor metabolism (Golder, 2007).

As used herein "mobility" refers to any ability relating to walking, walking speed, gait, strength of leg muscles, leg function and the ability to move with or without assistance. Mobility can be evaluated by one or more of several tests including but not limited to Ambulation Index, Time 25 foot walk, Six-Minute Walk (6MW), Lower Extremity Manual Muscle Test (LEMMT) and EDSS. Mobility can also be reported by the subject, for example by questionnaires, including but not limited to 12-Item Multiple Sclerosis Walking Scale (MSWS-12). Impaired Mobility refers to any impairment, difficulty or disability relating to mobility.

"T1-weighted MRI image" refers to an MR-image that emphasizes T1 contrast by which lesions may be visualized. Abnormal areas in a T1-weighted MRI image are "hypointense" and appear as dark spots. These spots are generally older lesions.

"T2-weighted MRI image" refers to an MR-image that emphasizes T2 contrast by which lesions may be visualized. T2 lesions represent new inflammatory activity.

The "Six-Minute Walk (6MW) Test" is a commonly used test developed to assess exercise capacity in patients with COPD (Guyatt, 1985). It has been used also to measure mobility in multiple sclerosis patients (Clinical Trials Website).

The "Timed-25 Foot Walk" or "T25-FW" is a quantitative mobility and leg function performance test based on a timed 25-walk. The patient is directed to one end of a clearly marked 25-foot course and is instructed to walk 25 feet as quickly as possible, but safely. The time is calculated from the initiation of the instruction to start and ends when the patient has reached the 25-foot mark. The task is immediately administered again by having the patient walk back the same distance. Patients may use assistive devices when doing this task. The score for the T25-FW is the average of the two completed trials. This score can be used individually or used as part of the MSFC composite score (National MS Society Website).

One of the central symptoms of multiple sclerosis is fatigue. Fatigue can be measured by several tests including but not limited to decrease of French valid versions of the Fatigue Impact Scale (EMIF-SEP) score, and European Quality of Life (EuroQoL) Questionnaire (EQ5D). Other tests, including but not limited to Clinician Global Impression of Change (CGIC) and Subject Global Impression (SGI), as well as EQ-5D, can be used to evaluate the general health status and quality of life of MS patients.

"Ambulation Index" or "AI" is a rating scale developed by Hauser et al. to assess mobility by evaluating the time and degree of assistance required to walk 25 feet. Scores range from 0 (asymptomatic and fully active) to 10 (bedridden). The patient is asked to walk a marked 25-foot course as quickly and safely as possible. The examiner records the time and type of assistance (e.g., cane, walker, crutches) needed. (Hauser, 1983)

"EQ-5D" is a standardized questionnaire instrument for use as a measure of health outcome applicable to a range of health conditions and treatments. It provides a simple descriptive profile and a single index value for health status that can be used in the clinical and economic evaluation of health care as well as population health surveys. EQ-5D was developed by the "EuroQoL" Group which comprises a network of international, multilingual, multidisciplinary researchers, originally from seven centers in England, Finland, the Netherlands, Norway and Sweden. The EQ-5D questionnaire is in the public domain and can be obtained from EuroQoL.

"SF-36" is a multi-purpose, short-form health survey with 36 questions which yields an 8-scale profile of functional health and well-being scores as well as psychometrically-based physical and mental health summary measures and a preference-based health utility index. It is a generic measure, as opposed to one that targets a specific age, disease, or treatment group. The survey is developed by and can be obtained from QualityMetric, Inc. of Providence, R.I.

A "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

It is understood that where a parameter range is provided, all integers within that range, and tenths thereof, are also provided by the invention. For example, "0.1-2.5 mg/day" includes 0.1 mg/day, 0.2 mg/day, 0.3 mg/day, etc. up to 2.5 mg/day.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Assessment of Efficacy of Laquinimod Alone or in-Combination with Fingolimod in MOG-Induced EAE In this experiment, MOG-induced EAE Mice were treated with a sub-optimal dose of laquinimod (10 mg/kg) alone or with add on fingolimod (0.3 mg/kg) to assess the efficacy of laquinimod alone or in combination with fingolimod. MOG-induced Experimental Autoimmune Encephalomyelitis (EAE) in the C57Bl strain of mice is an established EAE model to test the efficacy of candidate molecules for MS treatment.

The dosages were chosen based on known effective dose amounts for laquinimod (0.6 mg/day) and for fingolimod (0.5 mg/day) in humans (FDA News Release, 2010; U.S. Patent Application Publication 2010-0322900). The National Institutes of Health (NIH) provides a table of Equivalent Surface Area Dosage Conversion Factors below (Table 1) which provides conversion factors that account for surface area to weight ratios between species.

TABLE 1

Equivalent Surface Area Dosage Conversion Factors

| | | To | | | | |
|---|---|---|---|---|---|---|
| | | Mouse 20 g | Rat 150 g | Monkey 3 kg | Dog 8 kg | Man 60 kg |
| FROM | Mouse | 1 | ½ | ¼ | ⅙ | 1/12 |
| | Rat | 2 | 1 | ½ | ¼ | 1/7 |
| | Monkey | 4 | 2 | 1 | ⅗ | ⅓ |
| | Dog | 6 | 4 | 1⅔ | 1 | ½ |
| | Man | 12 | 7 | 3 | 2 | 1 |

Accordingly, the data from this mice study is representative of what can be expected in human patients with the treatment of laquinimod and fingolimod at the corresponding human dosages.

Procedure

Disease was induced in all mice by the injection of the encephalitogenic emulsion (MOG/CFA) and intraperitoneal injection of pertussis toxin on the first day and 48 hours later.

Fingolimod at dose levels of 0.3 (sub optimal) and 1 mg/kg (optimal) were administered by the oral dose, once daily (QD).

Laquinimod at dose levels of 10 (sub optimal) and 25 mg/kg (optimal) were administered by the oral route, once daily (QD).

Both fingolimod and laquinimod were administered prophylactic from disease induction—Day 1 until termination of the study.

Induction of EAE:

EAE was induced by subcutaneous injection of encephalitogenic emulsion at a volume of 0.2 ml/mouse in the right flank. On the day of induction, pertussis toxin was injected i.p. at a volume dose of 0.2 ml/mouse. The injection of the pertussis toxin was repeated after 48 hours.

Test Procedure:

Day 0: Subcutaneous injection of MOG into right flank, i.p. injection of Pertussis toxin, beginning of daily laquinimod treatment.

Day 2: i.p. injection of Pertussis toxin.

Day 10: Initiation of scoring of mice for EAE clinical signs.
Day 30: Termination of study.
Materials:
1. Fingolimod
2. Laquinimod
3. *Mycobacterium tuberculosis* (MT), Difco
4. Pertussis toxin, Sigma
5. MOG 35-55, Mnf Novatide
6. Complete Freund's Adjuvant (CFA), Sigma
7. Saline, Mnf-DEMO S.A
8. Sterile double distilled water (DDW)

Experimental Animals:
Healthy, nulliparous, non-pregnant female mice of the C57BL/6 strain were used in the study.
The animals weighed 18-22 grams, and were approximately 8 weeks old on receipt.
The body weights of the animals were recorded on the day of delivery.
Overtly healthy animals were assigned to study groups arbitrarily before treatment commenced.
The mice were individually identified by using ear tags. A color-coded card on each cage gave information including cage number, group number and identification.

EAE Induction:
EAE was induced by injecting the encephalitogenic mixture (emulsion) consisting of MOG (150.0 µg/mouse) and CFA containing *M. tuberculosis* (2 mg MT/mL CFA).
A volume of 0.2 ml of emulsion was injected subcutaneously into the flanks of the mice.
Pertussis toxin in 0.2 ml dosage volume was injected intraperitoneally on the day of induction and 48 hours later (total amount will be 0.1+0.1=0.2 µg/mouse).

Study Design:
The mice were allocated randomly into 6 groups according to Table 2 below.

| Group | Treatment Groups (treatment initiation) | dose/day | Administration Route | Regimen |
|---|---|---|---|---|
| 1 | Vehicle | 10 ml/kg | Oral, QD | Both fingolimod and laquinimod from Day 1 to 30 daily |
| 2 | laquinimod | 10 mg/kg | Oral, QD | |
| 2 | laquinimod | 25 mg/kg | Oral, QD | |
| 4 | fingolimod | 0.3 mg/kg | Oral, QD | |
| 5 | fingolimod | 1 mg/kg | Oral, QD | |
| 6 | laquinimod + fingolimod | 10 mg/kg + 0.3 mg/kg | Oral (QD) + Oral (QD) | |

Preparation and Administration of Encephalitogenic Emulsion:
Oil Portion:
20 mg MT was added to 20 ml CFA to yield 1+1=2 mg/ml MT).
Liquid Portion:
15 mg MOG or equivalent was diluted in 10 ml Normal Saline to yield 1.5 mg/ml MOG stock solution.
The emulsion was made from equal parts of oil and liquid portions (1:1) in two syringes connected to each other with Leur lock to yield 0.75 mg/ml and 1 mg/ml MT. The emulsion was transferred to insulin syringe and 0.2 ml was injected to the right flank of each mouse. Dose=0.15 mg MOG and 0.2 mg MT/mouse.
Preparation and Administration of Pertussis Toxin:
50 µL Pertussis toxin (200 µg/ml) was added to 19.95 ml saline to yield 500 ng/ml. The pertussis toxin was administered intraperitoneally on the day of encephalitogen injection and 48 hours later (100.0 ng/0.2 ml/mouse)—Total 200 ng/mouse.

Preparation and Administration of Test Articles
Fingolimod Formulations:
Fingolimod was weighed and sterile DDW was added to yield 0.03 and 0.1 mg/ml for dose levels of 0.3 and 1.0 mg/kg respectively. The mice were administered with the two concentrations of fingolimod (0.03 and 0.1 mg/ml) a volume dose level of 200 µl/mouse by the oral route for dose levels of 0.3 and 1.0 mg/kg respectively.

Laquinimod Formulations:
A concentration of 1.0 and 2.5 mg/ml laquinimod was prepared in DDW. The test formulations were stored at 2-8° C. until use in amber colored bottles.
The mice were administered with the two concentrations of laquinimod (1.0 and 2.5 mg/ml) a volume dose level of 200 µl/mouse by the oral route for dose levels of 10 and 25 mg/kg respectively.
Both the fingolimod and the laquinimod formulations were administered from Day 1, once daily (QD).
Six hours interval was maintained daily between administration of laquinimod and fingolimod.

EAE Clinical Signs:
The mice were observed daily from the 10th day post-EAE induction (first injection of MOG) and the EAE clinical signs were scored according to the grades described in the table presented below.

TABLE 3

Evaluation of the EAE clinical signs

| Score | Signs | Description |
|---|---|---|
| 0 | Normal behavior | No neurological signs. |
| 1 | Limp tail | Part or the whole tail is limp and droopy. |
| 2 | righting reflex | Animal has difficulties rolling onto his feet when laid on its back |
| 3 | Hind leg weakness | wobbly walk - when the mouse walks the hind legs are unsteady |
| 4 | Hind leg paralysis | The mouse drags its hind legs but is able to move around using its fore legs |
| 5 | Full paralysis | The mouse can't move around, it looks thinner and emaciated. |
| 6 | Moribund/Death | |

All mice with score 1 and above were considered sick. When the first clinical sign appears all mice were given food soaked in water, which was spread on different places on the bedding of the cages.

Interpretation of Results
Calculation of the Incidence of Disease (Disease Ratio)
The number of sick animals in each group were summed
The incidence of disease was calculated as $$\text{INCIDENCE of DISEASE} = \left(\frac{\text{No. of sick mice in treated group}}{\text{No. of sick mice in control group}}\right)$$

The percent inhibition according to incidence was calculated as $$\text{INHIBITION (\%) of INCIDENCE} = \left(1 - \frac{\text{Number of sick mice in treated group}}{\text{Number of sick mice in control group}}\right) \times 100$$

Calculation of the Mortality/Moribundity Rate (Mortality Ratio)

The number of dead or moribund animals in each group were summed

The mortality of disease was calculated as

MORTALITY of DISEASE =

$$\left(\frac{\text{No. of dead or } moribound \text{ mice in treated group}}{\text{No. of dead or } moribound \text{ mice in control group}}\right)$$

The percent inhibition according to mortality was calculated as

INHIBITION (%) of MORTALITY =

$$\left(1 - \frac{\text{Number of dead or } moribound \text{ mice in treated group}}{\text{Number of dead or } moribound \text{ mice in control group}}\right) \times 100$$

Calculation of Duration of Disease

The mean duration of disease expressed in days was calculated as $$\text{Mean Duration} = \left(\frac{\sum \text{Duration of disease of each mouse}}{\text{No. of mice in the group}}\right)$$

Calculation of Mean Delay in Onset of Disease

The mean onset of disease expressed in days was calculated as $$\text{Mean Onset} = \left(\frac{\sum \text{Onset of disease of each mouse}}{\text{No. of mice in the group}}\right)$$

The mean delay in onset of disease expressed in days was calculated by subtracting the mean onset of disease in control group from test group.

Calculation of the Mean Maximal Score and Percent Inhibition

The mean maximal score (MMS) of each group was calculated as $$MMS = \left(\frac{\sum \text{Maximal Score of each mouse}}{\text{No. of mice in the group}}\right)$$

The percent inhibition according to MMS was calculated as $$\text{INHIBITION (\%) of } MMS = \left(1 - \frac{MMS \text{ of treated group}}{MMS \text{ of control group}}\right) \times 100$$

Calculation of the Group Mean Score and Percent Inhibition

The daily scores of each mouse in the test group were summed and the individual mean daily score (IMS) was calculated as $$IMS = \left(\frac{\sum \text{Daily score of mouse}}{\text{Observation period (days)}}\right)$$

The mean group score (GMS) was calculated as $$GMS = \left(\frac{\sum IMS \text{ of each mouse}}{\text{No. of mice in the group}}\right)$$

The percent inhibition was calculated as $$\text{INHIBITION (\%) of } GMS = \left(1 - \frac{GMS \text{ of treated group}}{GMS \text{ of control group}}\right) \times 100$$

Results

A summary of the incidence, mortality, Group Mean Score (GMS), duration of the disease, onset of the disease and the activity of each group compared to the vehicle treated control group is shown in the Summarized Table 4. The Clinical profile of the treatment groups are presented graphically in FIG. 1.

In groups treated with fingolimod at dose levels of 0.3 mg/kg (sub optimal dose), and 1 mg/kg (optimal dose), 56.3 and 81.3% activity, respectively, was observed according to GMS when compared to the vehicle administered control group.

In groups treated with laquinimod at dose levels of 10 mg/kg (sub optimal dose), and 25 mg/kg (optimal dose), 53.1 and 81.1% activity, respectively, was observed according to GMS when compared to the vehicle administered control group.

The total blocking of EAE in the group treated with fingolimod at sub optimal dose level of 0.3 mg/kg in combination with sub optimal dose of laquinimod (10 mg/kg) exhibited activity superior to optimal dose of fingolimod (1 mg/kg) alone where 81.3% activity was observed and optimal dose of laquinimod (25 mg/kg) alone where 81.1% activity was observed according to GMS when compared to the vehicle administered control group.

TABLE 4

Test Article: laquinimod and fingolimod alone and in combination Mortality, incidence, GMS, Duration and Onset.

| Treatment | Mortality | Incidence | GMS value | Onset (days) | Duration (days) |
|---|---|---|---|---|---|
| Negative Control Vehicle 10 ml/kg | 1/15 | 15/15 | 3.2 ± 0.6 $p < 0.001$ | 9.1 ± 0.9 | 21.9 ± 0.9 |
| Laquinimod 10 mg/kg | 0/15 | 13/15 | 1.5 ± 0.8 $p < 0.001$ | 17.1 ± 6.3 $p < 0.001$ | 14.1 ± 6.4 $p < 0.001$ |
| Laquinimod 25 mg/kg | 0/15 | 7/15 | 0.6 ± 0.8 $p < 0.001$ | 22.9 ± 9.0 $p < 0.001$ | 8.1 ± 9.0 $p < 0.001$ |
| Fingolimod 0.3 mg/kg | 0/15 | 13/15 | 1.4 ± 0.8 $p < 0.001$ | 16.0 ± 6.7 $p < 0.001$ | 15.0 ± 6.7 $p < 0.001$ |
| Fingolimod 1 mg/kg | 0/15 | 8/15 | 0.6 ± 0.8 $p < 0.001$ | 21.7 ± 9.3 $p < 0.001$ | 7.59 ± 9.1 $p < 0.001$ |
| Laquinimod + Fingolimod 10 mg/kg + 0.3 mg/kg | 0/15 | 0/15 | 0.0 ± 0.0 $p < 0.001$ | 31.0 ± 0.0 $p < 0.001$ | 0.0 ± 0.0 $p < 0.001$ |

Conclusions

In this study, each compound alone showed a dose dependent inhibition of disease severity.

However, while the lower dosages tested (10 mg/kg laquinimod and 0.3 mg/kg fingolimod) were moderately effective individually, the combination of fingolimod and laquinimod when each was administered at its respective lower dosage was so potent that it completely abrogated disease. This unexpected result suggest that lower and suboptimal dosages of laquinimod and fingolimod can be used in combination to achieve a greater than additive therapeutic result, and provides evidence that such a combination can be used for therapeutic treatment of human MS and CIS patients.

Example 2

Assessment of Efficacy of Laquinimod as Add-On Therapy to Fingolimod in Multiple Sclerosis (MS) Patients Periodic oral administration of laquinimod (p.o. 0.6 mg/day or 1.2 mg/day) as an add-on therapy for a human patient afflicted with a form of MS who is already receiving fingolimod (p.o. 0.5 mg/day) provides a clinically meaningful advantage and is more effective (provides at least an additive effect or more than an additive effect) in treating the patient than when fingolimod is administered alone (at the same dose).

Periodic oral administration fingolimod (p.o. 0.5 mg/day) as an add-on therapy for a human patient afflicted with a form of MS who is already receiving of laquinimod (p.o. 0.6 mg/day or 1.2 mg/day) provides a clinically meaningful advantage and is more effective (provides at least an additive effect or more than an additive effect) in treating the patient than when laquinimod is administered alone (at the same dose).

The add-on therapies also provides efficacy (provides at least an additive effect or more than an additive effect) in treating the patient without undue adverse side effects or affecting the safety of the treatment. As compared to when each agent is administered alone:

1. The add-on therapy is more effective (provides an additive effect or more than an additive effect) in reducing the decrease in brain volume (determined by the percent brain volume change (PBVC)), in multiple sclerosis patients.
2. The add-on therapy is more effective (provides an additive effect or more than an additive effect) in increasing the time to confirmed disease progression (CDP), in multiple sclerosis patients, where CDP is defined as a sustained increase in EDSS of 1 point from Baseline for at least 3 months. Progression cannot be confirmed during a relapse.
3. The add-on therapy is more effective (provides an additive effect or more than an additive effect) in reducing abnormalities observed in whole Brain MTR histogram, in multiple sclerosis patients.
4. The add-on therapy is more effective (provides an additive effect or more than an additive effect) in reducing the number of confirmed relapses and therefore the relapse rate, in multiple sclerosis patients.
5. The add-on therapy is also more effective (provides an additive effect or more than an additive effect) in reducing the accumulation of physical disability in multiple sclerosis patients, as measured by the time to confirmed progression of EDSS.
6. The add-on therapy is more effective (provides an additive effect or more than an additive effect) in reducing MRI-monitored disease activity in multiple sclerosis patients, as measured by the cumulative number of T1 Gd-enhancing lesions on T1-weighted images, the cumulative number new T1 hypointense lesions, the cumulative number of new T2 lesions, the cumulative number of new T1 hypointense lesions on T1-weight images (black holes), the number of active (new T2 or GdE-T1) lesions, presence or absence of GdE lesions, change in total volume of T1 Gd-enhancing lesions, change in total volume of T2 lesions, and/or cortical thickness.
7. The add-on therapy is more effective (provides an additive effect or more than an additive effect) in reducing brain atrophy in multiple sclerosis patients.
8. The add-on therapy is more effective (provides an additive effect or more than an additive effect) in reducing the frequency of relapses, the frequency of clinical exacerbation, and the risk for confirmed progression in multiple sclerosis patients.
9. The add-on therapy is more effective (provides an additive effect or more than an additive effect) in increasing the time to confirmed relapse in multiple sclerosis patients.
10. The add-on therapy is more effective (provides an additive effect or more than an additive effect) in improving the general health status (as assessed by the EuroQoL (EQ5D) questionnaire), symptom severity on work (as assessed by the work productivity and activities impairment General Health (WPAI-GH) questionnaire) and quality of life, in multiple sclerosispatients.
11. The add-on therapy is more effective (provides an additive effect or more than an additive effect) in decreasing cerebral dysfunction/cognitive impairment (as assessed by Symbol Digit Modalities Test (SDMT)), in multiple sclerosis patients during the double blind study period.

Administration of laquinimod (p.o., 0.6 mg/day and 1.2 mg/day) as an add-on therapy to fingolimod (p.o., 0.5 mg/day) provides a clinically meaningful advantage and is more effective (provides an additive effect or more than an additive effect) in delaying the conversion to clinically definite MS in patients presenting a CIS suggestive of MS than when fingolimod is administered alone (at the same dose).

Administration of laquinimod (p.o., 0.6 mg/day and 1.2 mg/day) as an add-on therapy to fingolimod (p.o., 0.5 mg/day) provides a clinically meaningful advantage and is more effective (provides an additive effect or more than an additive effect) in reducing the rate of development of clinically definite MS, the occurrence of new MRI-detected lesions in the brain, the accumulation of lesion area in the brain and brain atrophy in persons at high risk for developing MS, and is more effective in reducing the occurrence of clinically definite MS and preventing irreversible brain damage in these persons than when fingolimod is administered alone (at the same dose).

Administration of fingolimod (p.o., 0.5 mg/day) as an add-on therapy to laquinimod (p.o., 0.6 mg/day and 1.2 mg/day) provides a clinically meaningful advantage and is more effective (provides an additive effect or more than an additive effect) in delaying the conversion to clinically definite MS in patients presenting a CIS suggestive of MS than when laquinimod is administered alone (at the same dose).

Administration of fingolimod (p.o., 0.5 mg/day) as an add-on therapy to laquinimod (p.o., 0.6 mg/day and 1.2 mg/day) provides a clinically meaningful advantage and is more effective (provides an additive effect or more than an additive effect) in reducing the rate of development of clinically definite MS, the occurrence of new MRI-detected lesions in the brain, the accumulation of lesion area in the brain and brain atrophy in persons at high risk for developing MS, and is more effective in reducing the occurrence of clinically definite MS and preventing irreversible brain damage in these persons than when laquinimod is administered alone (at the same dose).

Example 3

Assessment of Efficacy of Laquinimod in Combination with Fingolimod in Multiple Sclerosis (MS) Patients Periodic oral administration of laquinimod (0.6 mg/day or 1.2 mg/day) in combination with fingolimod (p.o., 0.5 mg/day) to a human patient afflicted with relapsing form of multiple sclerosis provides increased efficacy (provides at least an additive effect or more than an additive effect) in treating the patient than when laquinimod is administered alone or when fingolimod is administered alone (at the same dose). The combination therapy also provides efficacy (provides at least an additive effect or more than an additive effect) in treating the patient without undue adverse side effects or affecting the safety of the treatment.

The combination therapy provides a clinically meaningful advantage and is more effective (provides at least an additive effect or more than an additive effect) in treating the patient than when laquinimod or fingolimod is administered alone (at the same dose) in the following manner:

1. The combination therapy is more effective (provides an additive effect or more than an additive effect) in reducing the decrease in brain volume (determined by the percent brain volume change (PBVC)), in multiple sclerosis patients.
2. The combination therapy is more effective (provides an additive effect or more than an additive effect) in increasing the time to confirmed disease progression (CDP), in multiple sclerosis patients, where CDP is defined as a sustained increase in EDSS of 1 point from Baseline for at least 3 months. Progression cannot be confirmed during a relapse.
3. The combination therapy is more effective (provides an additive effect or more than an additive effect) in reducing abnormalities observed in whole Brain MTR histogram, in multiple sclerosis patients during.
4. The combination therapy is more effective (provides an additive effect or more than an additive effect) in reducing the number of confirmed relapses and therefore the relapse rate, in multiple sclerosis patients.
5. The combination therapy is also more effective (provides an additive effect or more than an additive effect) in reducing the accumulation of physical disability in multiple sclerosis patients, as measured by the time to confirmed progression of EDSS.
6. The combination therapy is more effective (provides an additive effect or more than an additive effect) in reducing MRI-monitored disease activity in multiple sclerosis patients, as measured by the cumulative number of T1 Gd-enhancing lesions on T1-weighted images, the cumulative number new T1 hypointense lesions, the cumulative number of new T2 lesions, the cumulative number of new T1 hypointense lesions on T1-weight images (black holes), the number of active (new T2 or GdE-T1) lesions, presence or absence of GdE lesions, change in total volume of T1 Gd-enhancing lesions, change in total volume of T2 lesions, and/or cortical thickness.
7. The combination therapy is more effective (provides an additive effect or more than an additive effect) in reducing brain atrophy in multiple sclerosis patients.
8. The combination therapy is more effective (provides an additive effect or more than an additive effect) in reducing the frequency of relapses, the frequency of clinical exacerbation, and the risk for confirmed progression in multiple sclerosis patients.
9. The combination therapy is more effective (provides an additive effect or more than an additive effect) in increasing the time to confirmed relapse in multiple sclerosis patients.
10. The combination therapy is more effective (provides an additive effect or more than an additive effect) in improving the general health status (as assessed by the EuroQoL (EQ5D) questionnaire), symptom severity on work (as assessed by the work productivity and activities impairment General Health (WPAI-GH) questionnaire) and quality of life, in multiple sclerosis patients.
11. The combination therapy is more effective (provides an additive effect or more than an additive effect) in decreasing cerebral dysfunction/cognitive impairment (as assessed by Symbol Digit Modalities Test (SDMT)), in multiple sclerosis patients during the double blind study period.

Administration of laquinimod (p.o., 0.6 mg/day and 1.2 mg/day) in combination with fingolimod (p.o., 0.5 mg/day) provides a clinically meaningful advantage and is more effective (provides an additive effect or more than an additive effect) in delaying the conversion to clinically definite MS in patients presenting a CIS suggestive of MS than when fingolimod is administered alone (at the same dose).

Administration of laquinimod (p.o., 0.6 mg/day and 1.2 mg/day) in combination with fingolimod (p.o., 0.5 mg/day) provides a clinically meaningful advantage and is more effective (provides an additive effect or more than an additive effect) in reducing the rate of development of clinically definite MS, the occurrence of new MRI-detected lesions in the brain, the accumulation of lesion area in the brain and brain atrophy in persons at high risk for developing MS, and is more effective in reducing the occurrence of clinically definite MS and preventing irreversible brain damage in these persons than when fingolimod is administered alone (at the same dose).

REFERENCES

1. "COPAXONE®" in *Physician's Desk Reference*, Thompson Reuters—Physician's Desk Reference Inc., Montvale, N.J., 2008, 3110-3113.
2. "FDA approves first oral drug to reduce MS relapses" FDA NEWS RELEASE, Sep. 22, 2010.
3. Alejandro Horga; Xavier Montalban Jun. 4, 2008; Expert Rev Neurother. 2008; 8(5):699-714.
4. Barkhof, F. (1999) "MRI in Multiple Sclerosis: Correlation with Expanded Disability Status Scale (EDSS)", *Multiple Sclerosis*. 5(4):283-286 (Abstract).
5. Berdyshev et al. (2009). "FTY720 inhibits ceramide synthases and up-regulates dihydrosphingosine 1-phosphate formation in human lung endothelial cells.". *Journal of Biological Chemistry* 284 (9): 5467-77.
6. Billich A et al. (2003). "Phosphorylation of the immunomodulatory drug FTY720 by sphingosine kinases". *J Biol Chem* 278 (48): 47408-15.
7. Bjartmar C and Fox R I. (2002) "Pathological mechanisms and disease progression of multiple sclerosis: therapeutic implication", *Drugs of Today*. 38:7-29.
8. Brex et al., (2002) "A longitudinal study of abnormalities on MRI and disability from multiple sclerosis", *N Engl J. Med. Jan.* 17, 2002 346(3):158-64.
9. Brod et al. (2000) Annals of Neurology, 47:127-131.
10. Brück (2011) "Insight into the mechanism of laquinimod action." *J Neurol Sci.* 2011 Jul. 15; 306(1-2):173-9.
11. Brunmark C et al., (2002) "The new orally active immunoregulator laquinimod (ABR-215062) effectively inhibits development and relapses of experimental autoimmune encephalomyelitis", *J Neuroimmunology.* 130:163-172.
12. Chabot and Yong, Interferon-1b increases IL-10 in a model of T cell-microglia interaction: Relevance to MS, *Neurol.* 2000, 55: 1497-1505.
13. Chabot et al., Cytokine production in T lymphocyte-microglia interaction is attenuated by glatiramer acetate: A mechanism for therapeutic efficacy in multiple sclerosis, *Mult. Scler.*, in press.
14. Clinical Trials Website, article entitled "Study of Fampridine-ER Tablets in Patients With Multiple Sclerosis", retrieved Jul. 10, 2012, <http://clinicaltrials.gov/ct2/show?term=fampridine&cond=multiple+sclerosis&phase=2 &rank=7>.
15. Comi et al. (2007) LAQ/5062 Study Group. "The Effect of Two Doses of Laquinimod on MRI-Monitored Disease Activity in Patients with Relapsing-Remitting Multiple Sclerosis: A Multi-Center, Randomized, Double-Blind, Placebo-Controlled Study", Presented at: 59*th Annual Meeting of the American Academy of Neurology*; Apr. 28-May 5, 2007; Boston, Mass.
16. Compston, Genetic susceptibility to multiple sclerosis, in *McAlpine's Mutiple Sclerosis*, Matthews, B. ed., London: Churchill Livingstone, 1991, 301-319.
17. Conway and Cohen (2010) "Combination therapy in multiple sclerosis", *LancetNeurol,* 9:299-308.
18. Costello et al. (2007) "Combination therapies for multiple sclerosis: scientific rationale, clinical trials, and clinical practice", *Current Opinion in Neurology,* 20:281-285.
19. Dal Canto et al. (1977) Multiple sclerosis. Animal model: Theiler's virus infection in mice. *Am. J. Path.* 88:497-500.
20. De Stefano et al. (1999) "Evidence of early axonal damage in patients with multiple sclerosis", Neurology. 52(Suppl 2):A378.
21. Dunitz, M. Multiple sclerosis therapeutics, Ed. Rudick and Goodkin. London: Taylor & Francis, 1999.
22. Durelli et al. and the Independent Comparison of Interferon (INCOMIN) Trial Study Group. (2002) "Every-other-day interferon beta-1b versus once-weekly interferon beta-1a for multiple sclerosis: results of a 2-year prospective randomised multicentre study (INCOMIN)", *Lancet.* 359:1453-60.
23. EMEA Guideline on Clinical Investigation of Medicinal Products for the Treatment of Multiple Sclerosis (CPMP/EWP/561/98 Rev. 1, November 2006).
24. EPAR, Rebif®, Scientific Discussion.
25. Fernández (2007) "Combination therapy in multiple sclerosis", *Journal of the neurological sciences,* 259:95-103.
26. Filippi et al., Glatiramer acetate reduces the proportion of MS lesions evolving into black holes, *Neurol.,* 2001, 57:731-733.
27. Fischer et al., (1999) "The Multiple Sclerosis Functional Composite measure (MSFC): an integrated approach to MS clinical outcome assessment" *Multiple Sclerosis,* 5(4): 244-250.
28. Fisk et al., (1994) "Measuring the Functional Impact of Fatigue: Initial Validation of Fatigue Impact Scale", *Clin Inf Dis.* 18 Suppl 1:S79-83.
29. Fisk et al., (1994) "The Impact of Fatigue on Patients with Multiple Sclerosis", *Can J Neurol Sci.* 21:9-14.
30. Frenández (2007) "Combination therapy in multiple sclerosis", *Journal of the neurological sciences,* 259:95-103.
31. Frohman et al., (2003) "The utility of MRI in suspected MS: report of the Therapeutics and Technology Assessment Subcommittee of the American Academy of Neurology", *Neurology. Sep.* 9, 2003, 61(5):602-11.
32. Gold (2008) "Combination therapies in multiple sclerosis", *J Neurol,* 255[Suppl 1]:51-60.
33. Golder W, (2007) "Magnetic resonance spectroscopy in clinical oncology", *Onkologie.* 27(3): 304-9.
34. Grossman et al., (1994) Magnetization transfer: theory and clinical applications in neuroradiology", *RadioGraphics.* 14:279-290.
35. Guidance for Industry. In vivo drug metabolism/drug interaction studies—study design, data analysis, and recommendations for dosing and labeling, U.S. Dept. Health and Human Svcs., FDA, Ctr. for Drug Eval. and Res., Ctr. For Biologics Eval. and Res., Clin./Pharm., November 1999 <http://www.fda.gov/cber/gdlns/metabol.pdf>.
36. Gurevich et al. (2010) "Laquinimod suppress antigen presentation in relapsing-remitting multiple sclerosis: in vitro high-throughput gene expression study" (J Neuroimmunol 2010 Apr. 15; 221(1-2):87-94. Epub 2010 Mar. 27.
37. Guyatt et al. (1985) "The 6-minute walk: a new measure of exercise capacity in patients with chronic heart failure", *Can Med Assoc J.,* 132:919-823.
38. Hafler and Weiner, M S: A CNS and systemic autoimmune disease, *Immunol. Today,* 1989, 10:104-107.
39. Hartung et al. (2005) "Significance of neutralizing antibodies to interferon beta during treatment of multiple sclerosis: expert opinions based on the Proceedings of an International Consensus Conference", *Eur J. Neurol.* 12:588-601.
40. Hauser et al. (1983) "Intensive immunosuppression in progressive multiple sclerosis", *New Engl J. Med.* 308: 173-180.
41. Hla T, Lee M J, Ancellin N, Paik J H, Kluk M J (2001). "Lysophospholipids—receptor revelations". *Science* 294 (5548): 1875-8.
42. Hohlfeld et al. (2000) "The neuroprotective effect of inflammation: implications for the therapy of multiple sclerosis", J. Neuroimmunol. 107:161-166.
43. Johnson et al., Copolymer 1 reduces relapse rate and improves disability in relapsing-remitting multiple sclerosis: results of a phase III multicenter, double-blind placebo-controlled trial. The Copolymer 1 Multiple Sclerosis Study Group, *Neurol.,* 1995, 45:1268.
44. Kleinschmidt-DeMasters et al. (2005) New England Journal of Medicine, 353:369-379.
45. Kurtzke J F, (1983) "Rating neurologic impairment in multiple sclerosis: an expanded disability status scale (EDSS)", *Neurology* 33(11):1444-1452.
46. Lampert, Autoimmune and virus-induced demyelinating diseases. A review, *Am. J. Path.,* 1978, 91:176-208.
47. Langer-Gould et al. (2005) *New England Journal of Medicine,* 353:369-379.
48. Lublin F D, Reingold S C (1996) "Defining the clinical course of multiple sclerosis", *Neurol.* 46:907-911.
49. Martyn, The epidemiology of multiple sclerosis, in *McAlpine's Multiple Sclerosis*, Matthews, B., ed., London: Churchil Livingstone, 1991, 3-40.
50. McDonald et al., Recommended diagnostic criteria for multiple sclerosis: guidelines from the International Panel on the diagnosis of multiple sclerosis. *Ann. Neurol.,* 2001, 50:121-127.
51. McDonald, (2001) "Guidelines from the International Panel on the Diagnosis of Multiple Sclerosis" Ann. Neurol. 50:121-127.
52. Mehta et al. (1996) "Magnetization transfer magnetic resonance imaging: a clinical review", *Topics in Magnetic Resonance Imaging* 8(4):214-30.
53. Miki et al. (1999) "Relapsing-Remitting Multiple Sclerosis: Longitudinal Analysis of MR Images—Lack of Correlation between Changes in T2 Lesion Volume and Clinical Findings", *Radiology.* 213:395-399.
54. Milo and Panitch (2011) "Combination therapy in multiple sclerosis", *Journal of Neuroimmunology,* 231 (2011): 23-31.
55. Moraal et al. (2008) "Subtraction MR Images in a Multiple Sclerosis Multicenter Clinical Trial Setting", *Radiology,* 250(2):506-514.
56. Multiple sclerosis: its diagnosis, symptoms, types and stages, 2003 <http://www.albany.net/~tjc/multiple-sclerosis.html>.
57. National MS Society Website, retrieved Jul. 10, 2012 <http://www.nationalmssociety.org/for-professionals/researchers/clinical-study-measures/t25-
58. Neuhaus et al. (2003) "Immunomodulation in multiple sclerosis: from immunosuppression to neuroprotection", Trends Pharmacol Sci. 24:131-138.
59. Noseworthy et al. (2000) "Multiple sclerosis", N Engl J. Med. 343:938-952.
60. Olsson, Immunology of multiple sclerosis, *Curr. Opin. Neurol. Neurosurg.,* 1992, 5:195-202.
61. Panitch et al. for the EVIDENCE (Evidence of Interferon Dose-response: European North American Comparative Efficacy) Study Group and the University of British Columbia MS/MRI Research Group. (2002) "Randomized comparative study of interferon β-1a treatment regiments in MS", The EVIDENCE Trial. Neurology. 59:1496-1506.
62. Parkman, Graft-versus-host Disease, *Ann. Rev. Med.,* 1991, 42: 189-197.
63. Paugh S W, et al. (2006). "Sphingosine and its analog, the immunosuppressant 2-amino-2-(2-[4-octylphenyl]ethyl)-1,3-propanediol, interact with the CB1 cannabinoid receptor.". *Mol. Pharmacol.* 70 (1): 41-50.
64. Paugh S W et al. (2003). "The immunosuppressant FTY720 is phosphorylated by sphingosine kinase type 2". *FEBS Lett* 554 (1-2): 189-93.
65. Payne S G, Oskeritzian C A, Griffiths R, Subramanian P, Barbour S E, Chalfant C E, Milstien S, Spiegel S. (2007). "The immunosuppressant drug FTY720 inhibits cytosolic phospholipase A2 independently of sphingosine-1-phosphate receptors.". *Blood* 109 (3): 1077-85. doi:10.1182/blood-2006-03-011437.
66. PCT International Application Publication No. WO 1998/30227, published Jul. 16, 1998.
67. PCT International Application Publication No. WO 2000/05250, published Feb. 3, 2000.
68. PCT International Application Publication No. WO 2000/18794, published Apr. 6, 2000.
69. PCT International Application Publication No. WO 2003/048735, published Jun. 12, 2003.
70. PCT International Application Publication No. WO 2004/103297, published Dec. 2, 2004.
71. PCT International Application Publication No. WO 2006/016036, published Nov. 2, 2006.
72. PCT International Application Publication No. WO 2006/029393, published Mar. 16, 2006.
73. PCT International Application Publication No. WO 2006/029411, published Mar. 16, 2006.
74. PCT International Application Publication No. WO 2006/083608, published Aug. 10, 2006.
75. PCT International Application Publication No. WO 2006/089164, published Aug. 24, 2006.
76. PCT International Application Publication No. WO 2006/116602, published Nov. 2, 2006.
77. PCT International Application Publication No. WO 2007/047863, published Apr. 26, 2007.
78. PCT International Application Publication No. WO 2007/146248, published Dec. 21, 2007, international filing date Jun. 12, 2007.
79. PCT International Application Publication No. WO 2009/070298, published Jun. 4, 2009.
80. PCT International Application Publication No. WO 2011/008274, published Jan. 20, 2011.
81. PCT International Application Publication No. WO 2011/022063, published Feb. 24, 2011.
82. PCT International Application Publication No. WO 2012/051106, published Apr. 19, 2012.
83. Polman et al. (2011) "Diagnostic Criteria for Multiple Sclerosis: 2010 Revisions to the McDonald Criteria", Ann Neural, 69:292-302.
84. Polman et al., (2005) "Diagnostic criteria for multiple sclerosis: 2005 revisions to the McDonald Criteria", Annals of Neurology, Volume 58 Issue 6, Pages 840-846.
85. Polman et al., (2005) "Treatment with laquinimod reduces development of active MRI lesions in relapsing MS", Neurology. 64:987-991.
86. Poser et al. (1983) "New Diagnostic Criteria for Multiple Sclerosis: Guidelines for Research Protocols", Annals of Neurology, March 1983, 13(3):227-230.
87. Rodriguez et al. (1987) Theiler's murine encephalomyelitis: a model of demyelination and persistence of virus. *Crit. Rev. Immunol.,* 7:325.
88. Rosen Y, (2007) "The Recent advances in magnetic resonance neurospectroscopy", *Neurotherapeutics.* 27(3):330-45.
89. RTT News Article dated April 12, 11, entitled "Teva Pharma, Active Biotech Post Positive Laquinimod Phase 3 ALLEGRO Results".
90. Rudick et al. (2006) *New England Journal of Medicine,* 354:911-923.
91. Rudick, R. (1999) "Disease-Modifying Drugs for Relapsing-Remitting Multiple Sclerosis and Future Directions for Multiple Sclerosis Therapeutics", *Neurotherpatueics.* 56:1079-1084.
92. Runström et al. (2002) "Laquinimod (ABR-215062) a candidate drug for treatment of Multiple Sclerosis inhibits the development of experimental autoimmune encephalomyelitis in IFN-β knock-out mice", (Abstract), Medicon Valley Academy, Malmoe, Sweden.
93. Runström et al. (2006) "Inhibition of the development of chronic experimental autoimmune encephalomyelitis by laquinimod (ABR-215062) in IFN-β k.o. and wild type mice" *Journal of Neuroimmunology,* 173 (2006):69-78.
94. Salama et al. (2003) *Multiple Sclerosis,* 9:28-31.
95. Sanchez, T; Estrada-Hernandez, T; Paik, J H; Wu, M T; Venkataraman, K; Brinkmann, V; Claffey, K; Hla, T (2003). "Phosphorylation and action of the immunomodulator FTY720 inhibits vascular endothelial cell growth factor-induced vascular permeability." *The Journal of biological chemistry* 278 (47): 47281-90.
96. Sandberg-Wollheim et al. (2005) "48-week open safety study with high-dose oral laquinimod in patients", Mult Scler. 11:S154 (Abstract).
97. Sorenson P S. (2006) "Neutralising antibodies to interferon-β—measurement, clinical relevance, and management", *J. Neurol.* 253 [Suppl 6]:VI/16-VI/22.
98. Teitelbaum et al., Suppression of Experimental Allergic Encephalomyelitis by a Synthetic Polypeptide, *Eur. J. Immunol.,* 1971, 1: 242-248.
99. Teitelbaum et al., Suppression of Experimental Allergic Encephalomyelitis with Basic Polymers, *Eur. J. Immunol.,* 1973, 3: 273-279.

100. Teva Press Release dated Aug. 1, 2011, entitled "Results of Phase III BRAVO Trial Reinforce Unique Profile of Laquinimod for Multiple Sclerosis Treatment".
101. The National MS Society (USA), *The Disease Modifying Drug Brochure*, Oct. 19, 2006.
102. U.S. Patent Application Publication No. 2008-0207526, published Aug. 28, 2008 (Strominger et al.).
103. U.S. Patent Application Publication No. 2010-0322900, published Dec. 23, 2010 (Tarcic et al.).
104. U.S. Patent Application Publication No. 2011-0027219, published Feb. 3, 2011 (Tarcic et al.).
105. U.S. Patent Application Publication No. 2011-0034508, published Feb. 10, 2011 (Liat Hayardeny).
106. U.S. Patent Application Publication No. 2011-0217295, published Sep. 8, 2011 (Haviv and Tarcic).
107. U.S. Patent Application Publication No. 2011-0218179, published Sep. 8, 2011 (Haviv and Tarcic).
108. U.S. Patent Application Publication No. 2011-0218203, published Sep. 8, 2011 (Joel Kaye et al.).
109. U.S. Patent Application Publication No. 2011-0230413, published Sep. 22, 2011 (Suhayl Dhib-Jalbut).
110. U.S. Patent Application Publication No. 2012-0010238, published Jan. 12, 2012 (Fristedt).
111. U.S. Patent Application Publication No. 2012-0010239, published Jan. 12, 2012 (Piryatinsky et al.).
112. U.S. Patent Application Publication No. 2012-0142730, published Jun. 7, 2012 (Tarcic et al.).
113. U.S. Pat. No. 3,849,550, issued Nov. 19, 1974 (Teitelbaum et al).
114. U.S. Pat. No. 5,800,808, issued Sep. 1, 1998 (Konfino et al).
115. U.S. Pat. No. 5,858,964, issued Jan. 12, 1999 (Aharoni et al).
116. U.S. Pat. No. 5,981,589, issued Nov. 9, 1999 (Konfino et al).
117. U.S. Pat. No. 6,048,898, issued Apr. 11, 2000 (Konfino et al).
118. U.S. Pat. No. 6,054,430, issued Apr. 25, 2000 (Konfino et al).
119. U.S. Pat. No. 6,077,851, issued Jun. 20, 2000 (Bjork et al).
120. U.S. Pat. No. 6,214,791, issued Apr. 10, 2001 (Amon et al).
121. U.S. Pat. No. 6,342,476, issued Jan. 29, 2002 (Konfino et al).
122. U.S. Pat. No. 6,362,161, issued Mar. 26, 2002 (Konfino et al).
123. U.S. Pat. No. 7,566,767, issued Jul. 28, 2009 (Strominger et al.).
124. U.S. Pat. No. 7,589,208, issued Sep. 15, 2009 (Jansson et al).
125. U.S. Pat. No. 7,884,208, issued Feb. 8, 2011 (Frenkel et al.).
126. U.S. Pat. No. 7,989,473, issued Aug. 2, 2011 (Patashnik et al.).
127. U.S. Pat. No. 8,008,258, issued Aug. 30, 2011 (Aharoni et al).
128. U.S. Pat. No. 8,178,127, issued May 15, 2012 (Safadi et al.).
129. Vollmer et al. (2008) "Glatiramer acetate after induction therapy with mitoxantrone in relapsing multiple sclerosis" Multiple Sclerosis, 00:1-8.
130. Yang et al., (2004) "Laquinimod (ABR-215062) suppresses the development of experimental autoimmune encephalomyelitis, modulates the Th1/Th2 balance and induces the Th3 cytokine TGF-$\beta$ in Lewis rats", J. Neuroimmunol. 156:3-9.
131. Yong (2002) "Differential mechanisms of action of interferon-13 and glatiramer acetate in MS" *Neurology,* 59:1-7.
132. Zou et al. (2002) "Suppression of experimental autoimmune neuritis by ABR-215062 is associated with altered Th1/Th2 balance and inhibited migration of inflammatory cells into the peripheral nerve tissue", *Neuropharmacology.* 42:731.

What is claimed is:

1. A method of treating a subject afflicted with multiple sclerosis or presenting a clinically isolated syndrome comprising periodically administering to the subject an amount of laquinimod and an amount of fingolimod, wherein the amounts when taken together are effective to achieve a greater than additive therapeutic result in treating the subject.

2. The method of claim 1, wherein the amount of laquinimod and the amount of fingolimod when administered together is more effective to treat the subject than when each agent at the same amount is administered alone.

3. The method of claim 1, wherein the amount of laquinimod and the amount of fingolimod when taken together is effective to reduce a symptom of multiple sclerosis in the subject.

4. The method of claim 3, wherein the symptom is a MRI-monitored multiple sclerosis disease activity, relapse rate, accumulation of physical disability, frequency of relapses, decreased time to confirmed disease progression, decreased time to confirmed relapse, frequency of clinical exacerbation, brain atrophy, neuronal dysfunction, neuronal injury, neuronal degeneration, neuronal apoptosis, risk for confirmed progression, deterioration of visual function, fatigue, impaired mobility, cognitive impairment, reduction of brain volume, abnormalities observed in whole Brain MTR histogram, deterioration in general health status, functional status, quality of life, and/or symptom severity on work.

5. The method of claim 4, wherein the amount of laquinimod and the amount of fingolimod when taken together is effective to decrease or inhibit reduction of brain volume.

6. The method of claim 4, wherein the amount of laquinimod and the amount of fingolimod when taken together is effective to increase time to confirmed disease progression.

7. The method of claim 4, wherein the amount of laquinimod and the amount of fingolimod when taken together is effective to decrease abnormalities observed in whole Brain MTR histogram.

8. The method of claim 1, wherein laquinimod is laquinimod sodium.

9. The method of claim 1, wherein fingolimod is fingolimod hydrochloride.

10. The method of claim 1, wherein the laquinimod and/or the fingolimod is administered via oral administration.

11. The method of claim 1, wherein the laquinimod and/or the fingolimod is administered daily.

12. The method of claim 1, wherein the amount laquinimod administered is 0.1-40.0 mg/day.

13. The method of claim 12, wherein the amount laquinimod administered is 0.6 mg/day.

14. The method of claim 12, wherein the amount laquinimod administered is 1.2 mg/day.

15. The method of claim 1, wherein the amount fingolimod administered is 0.01-2.5 mg/day.

16. The method of claim 15, wherein the amount fingolimod administered is 0.5 mg/day.

17. A package comprising:
a) a first pharmaceutical composition comprising an amount of laquinimod and a pharmaceutically acceptable carrier;

b) a second pharmaceutical composition comprising an amount of fingolimod and a pharmaceutically acceptable carrier; and c) instructions for use of the first and second pharmaceutical compositions together to treat a subject afflicted with multiple sclerosis or presenting a clinically isolated syndrome.

18. A pharmaceutical composition consisting essentially of an amount of laquinimod and an amount of fingolimod.

19. A therapeutic package for dispensing to, or for use in dispensing to, a subject afflicted with multiple sclerosis or presenting a clinically isolated syndrome, which comprises:
  a) one or more unit doses, each such unit dose consisting essentially of:
    i) an amount of laquinimod; and
    ii) an amount of fingolimod,
  wherein the respective amounts of said laquinimod and said fingolimod in said unit dose are effective, upon concomitant administration to said subject, to achieve a greater than additive therapeutic result in treating the subject, and b) a finished pharmaceutical container therefor, said container containing said unit dose or unit doses, said container further containing or comprising labeling directing the use of said package in the treatment of said subject.

20. A pharmaceutical composition in unit dosage form, useful in treating a subject afflicted with multiple sclerosis or presenting a clinically isolated syndrome, which consists essentially of:
  a) an amount of laquinimod; and
  b) an amount of fingolimod,
  wherein the respective amounts of said laquinimod and said fingolimod in said composition are effective, upon concomitant administration to said subject of one or more of said unit dosage forms of said composition, to achieve a greater than additive therapeutic result in treating the subject.

* * * * *